(12) United States Patent
Nye et al.

(10) Patent No.: US 8,728,068 B2
(45) Date of Patent: May 20, 2014

(54) COOLED ANTENNA FOR DEVICE INSERTABLE INTO A BODY

(75) Inventors: Neil Nye, St. Anthony, MN (US); Eric Rudie, Maple Grove, MN (US); Jonathan Achenbach, New York, NY (US)

(73) Assignee: Urologix, Inc., Plymouth, MN (US)

( * ) Notice: Subject to any disclaimer, the term of this patent is extended or adjusted under 35 U.S.C. 154(b) by 791 days.

(21) Appl. No.: 12/757,670

(22) Filed: Apr. 9, 2010

(65) Prior Publication Data

US 2010/0262137 A1 Oct. 14, 2010

Related U.S. Application Data

(60) Provisional application No. 61/212,257, filed on Apr. 9, 2009.

(51) Int. Cl.
*A61B 18/18* (2006.01)

(52) U.S. Cl.
USPC ................................ 606/33; 606/27; 607/102

(58) Field of Classification Search
USPC ............ 606/22–28, 31, 33, 41; 607/101–102; 128/898
See application file for complete search history.

(56) References Cited

U.S. PATENT DOCUMENTS

| 5,300,099 | A | 4/1994 | Rudie |
| 5,348,554 | A | 9/1994 | Imran et al. |
| 5,496,271 | A * | 3/1996 | Burton et al. ................... 607/27 |
| 5,735,847 | A | 4/1998 | Gough et al. |
| 5,913,854 | A | 6/1999 | Maguire et al. |
| 6,277,113 | B1 * | 8/2001 | Berube .......................... 606/33 |
| 6,496,737 | B2 | 12/2002 | Rudie et al. |
| 6,514,251 | B1 | 2/2003 | Ni et al. |
| 6,986,769 | B2 | 1/2006 | Nelson et al. |
| 7,264,619 | B2 | 9/2007 | Venturelli |
| 7,311,703 | B2 | 12/2007 | Turovskiy et al. |
| 2001/0016761 | A1 * | 8/2001 | Rudie et al. .................. 607/101 |
| 2003/0065317 | A1 | 4/2003 | Rudie et al. |
| 2005/0245920 | A1 | 11/2005 | Vitullo |
| 2006/0079884 | A1 * | 4/2006 | Manzo et al. .................. 606/41 |
| 2008/0033424 | A1 | 2/2008 | van der Weide et al. |

* cited by examiner

*Primary Examiner* — Michael Peffley
*Assistant Examiner* — Khadijeh Vahdat
(74) *Attorney, Agent, or Firm* — Dicke, Billig & Czaja, PLLC

(57) ABSTRACT

A device for treating tissue adjacent to a body lumen includes a catheter shaft and an energy emitting assembly. The catheter shaft is insertable into the body lumen and includes a plurality of cooling lumens arranged generally circumjacent a generally central lumen. At least some of the circumjacent cooling lumens are in fluid communication with the central lumen and the energy emitting assembly extends through the central lumen. The central lumen and at least one portion of the energy emitting assembly are configured to direct a flow of cooling fluid about an outer surface of the at least one portion of the energy emitting assembly within the central lumen.

26 Claims, 20 Drawing Sheets

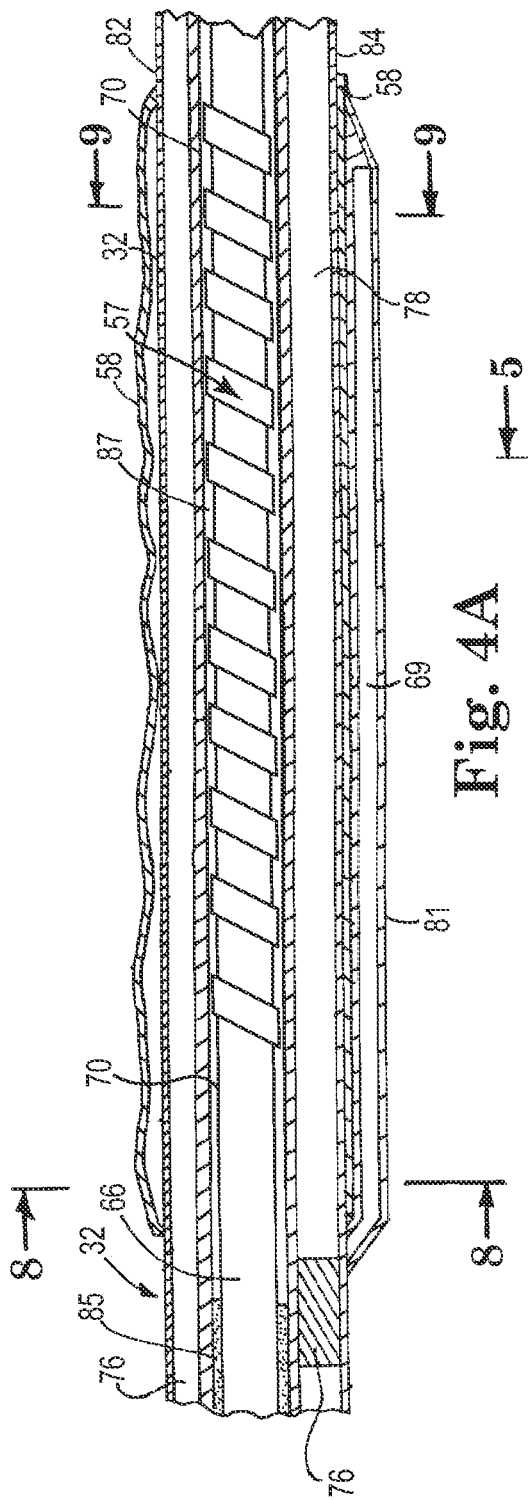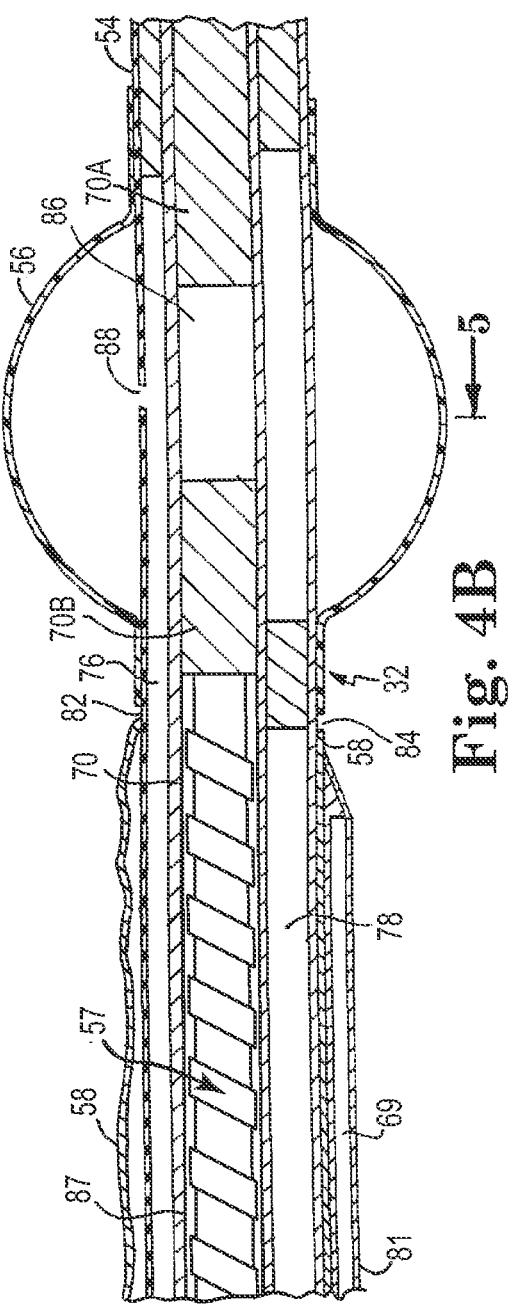

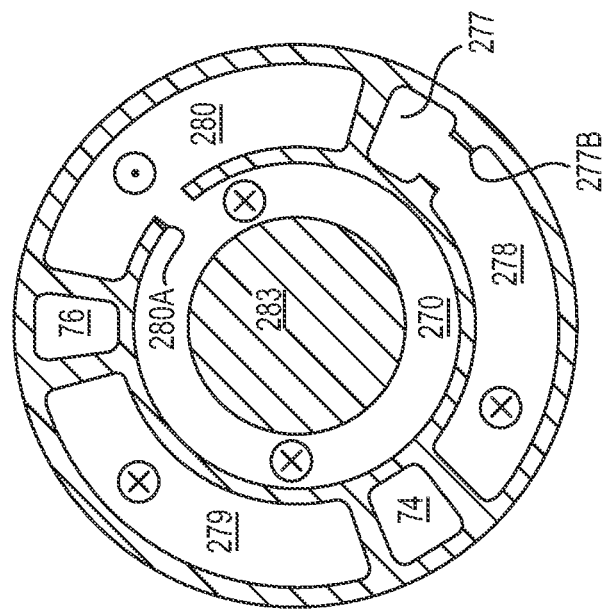
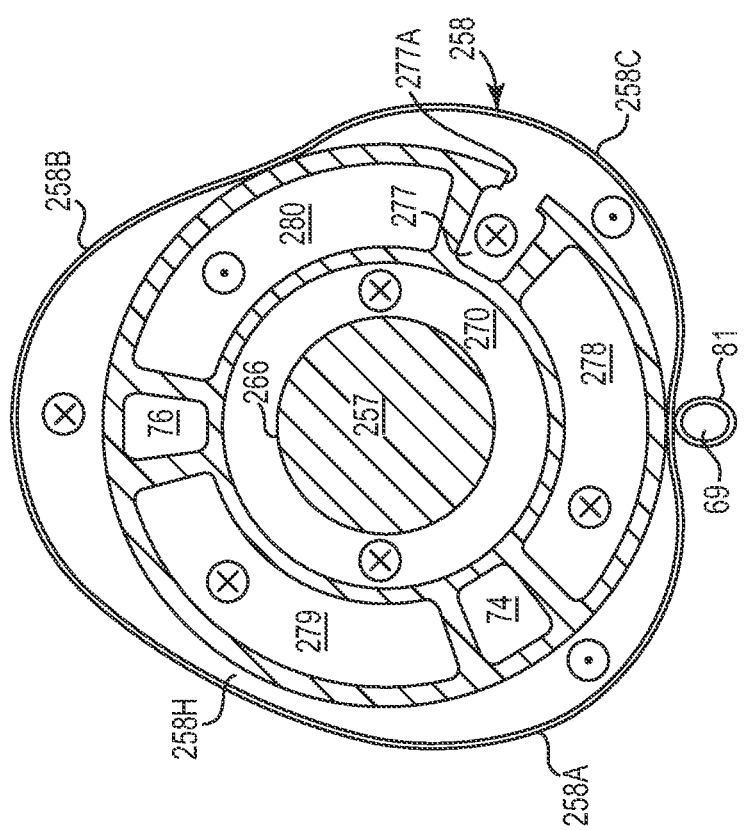
Fig. 19B
Fig. 19A

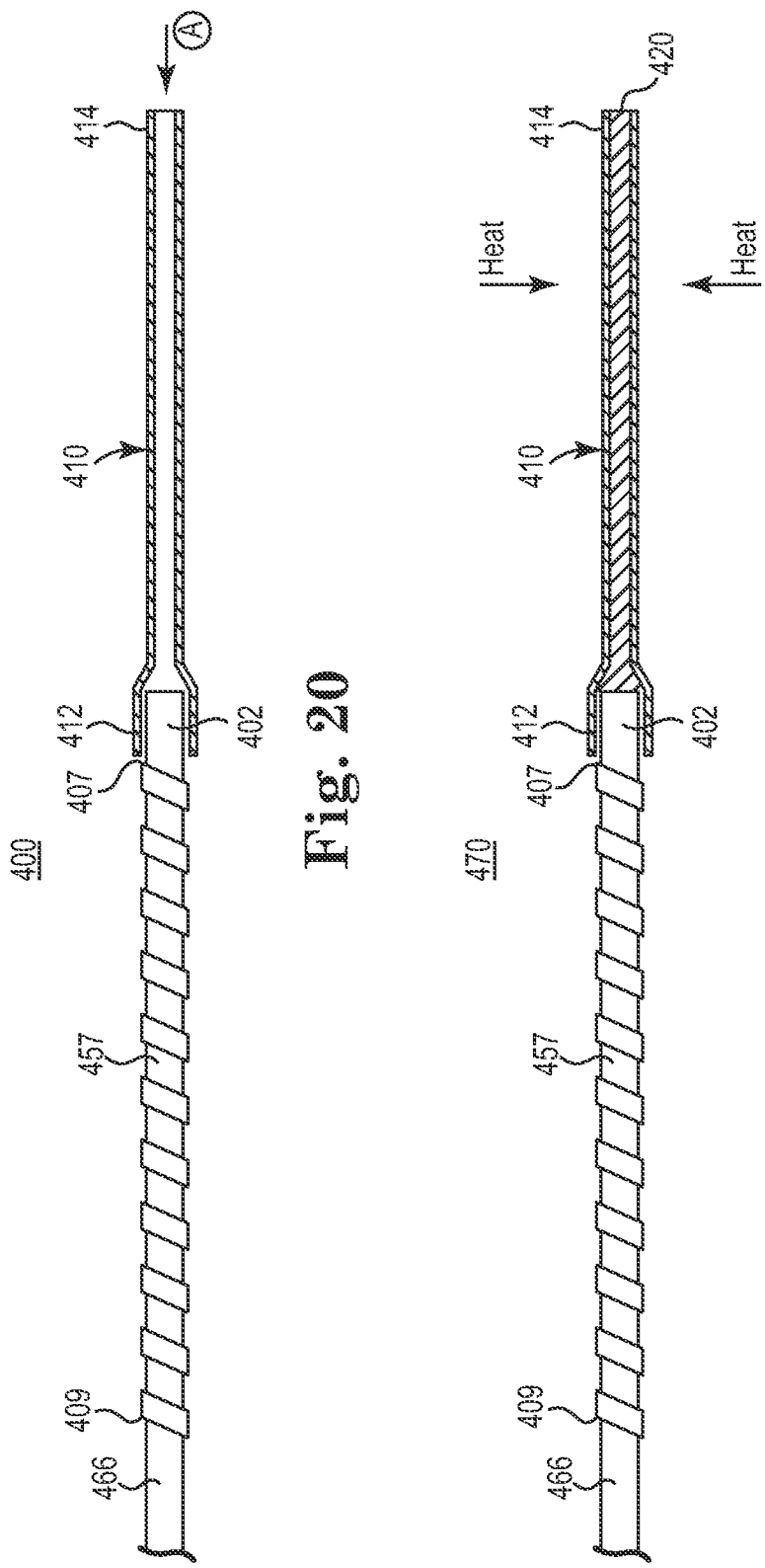

COOLED ANTENNA FOR DEVICE INSERTABLE INTO A BODY

CROSS REFERENCE TO RELATED APPLICATIONS

This application is a Non-Provisional Application that claims priority to Provisional U.S. Patent Application Ser. No. 61/212,257, entitled THERMAL THERAPY CATHETER, having a filing date of Apr. 9, 2009, and which is incorporated herein by reference

BACKGROUND

The prostate gland is a complex, chestnut-shaped organ which encircles the urethra immediately below the bladder. Nearly one third of the prostate tissue anterior to the urethra consists of fibromuscular tissue that is anatomically and functionally related to the urethra and the bladder. The remaining two thirds of the prostate is generally posterior to the urethra and is comprised of glandular tissue. The portion of the urethra extending through the prostate (i.e., the prostatic urethra) includes a proximal segment, which communicates with the bladder, and a distal segment, which extends at an angle relative to the proximal segment by the verumontanum.

Although a relatively small organ, the prostate is the most frequently diseased of all internal organs and is often the site of a common affliction among older men, benign prostatic hyperplasia (BPH), as well as a more serious affliction, cancer. BPH is a nonmalignant, bilateral expansion of prostate tissue occurring mainly in the transition zone of the prostate adjacent to the proximal segment of the prostatic urethra. As this tissue grows in volume, it encroaches on the urethra extending into the region of the bladder neck at the base of the bladder. Left untreated, BPH causes obstruction of the urethra which usually results in increased urinary frequency, urgency, incontinence, nocturia and slow or interrupted urinary stream. BPH may also result in more severe complications, such as urinary tract infection, acute urinary retention, hydronephrosis and uraemia.

Benign prostatic hyperplasia (BPH) may be treated using transurethral thermal therapy as described in further detail in U.S. Pat. No. 5,413,588 entitled DEVICE AND METHOD FOR ASYMMETRICAL THERMAL THERAPY WITH HELICAL DIPOLE MICROWAVE ANTENNA, in U.S. Pat. No. 5,575,811 entitled BENIGN PROSTATIC HYPERPLASIA TREATMENT CATHETER WITH URETHRAL COOLING, and in U.S. Pat. No. 6,496,737 entitled THERMAL THERAPY CATHETER, all of which are hereby incorporated by reference. During transurethral thermal therapy, the transition zone of the prostate is heated to necrose the tumorous tissue that encroaches on the urethra. Transurethral thermal therapy is administered by use of a microwave antenna-containing catheter which includes a multi-lumen shaft. The catheter is positioned in the urethra with the microwave antenna located adjacent to the hyperplastic prostatic tissue. Energization of the microwave antenna causes the antenna to emit electromagnetic energy which heats tissue within the prostate. A cooling fluid is circulated through the catheter to preserve tissue such as the urethral wall between the microwave antenna and the target tissue of the prostate.

The commercially available Cooled ThermoCath (CTC) system from Urologix, Inc. of Minneapolis, Minn. employs a thermal therapy catheter that embodies the aforementioned U.S. Pat. No. 6,496,737, and is a product capable of performing thermal therapy of the prostate with microwave energy delivered from an applicator positioned in the urethra. The CTC system has achieved substantial clinical and commercial success, indicating the efficacy of microwave thermal therapy for treating prostate disease. This therapy is benefited by further developments in the technology of thermal therapy catheters to enhance the effects of microwave treatment of the prostate.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 4A is a cross-sectional view of a portion of the thermal therapy catheter in the vicinity of a multi-lobe balloon and microwave antenna, according to one embodiment of the present invention.

FIG. 4B is a cross-sectional view of a portion of the thermal therapy catheter in the vicinity of a retention balloon, according to one embodiment of the present invention.

FIG. 19A is a cross-sectional view, as taken along line 19A-19A of FIG. 16, of the thermal therapy catheter, according to one embodiment of the present invention.

FIG. 19B is a cross-sectional view, as taken along line 19B-19B of FIG. 16, of the thermal therapy catheter, according to one embodiment of the present invention.

FIGS. 20-24 are a series of partial sectional views of a partial antenna assembly in a method of forming a catheter, according to embodiments of the present invention.

DETAILED DESCRIPTION

Figure 1:
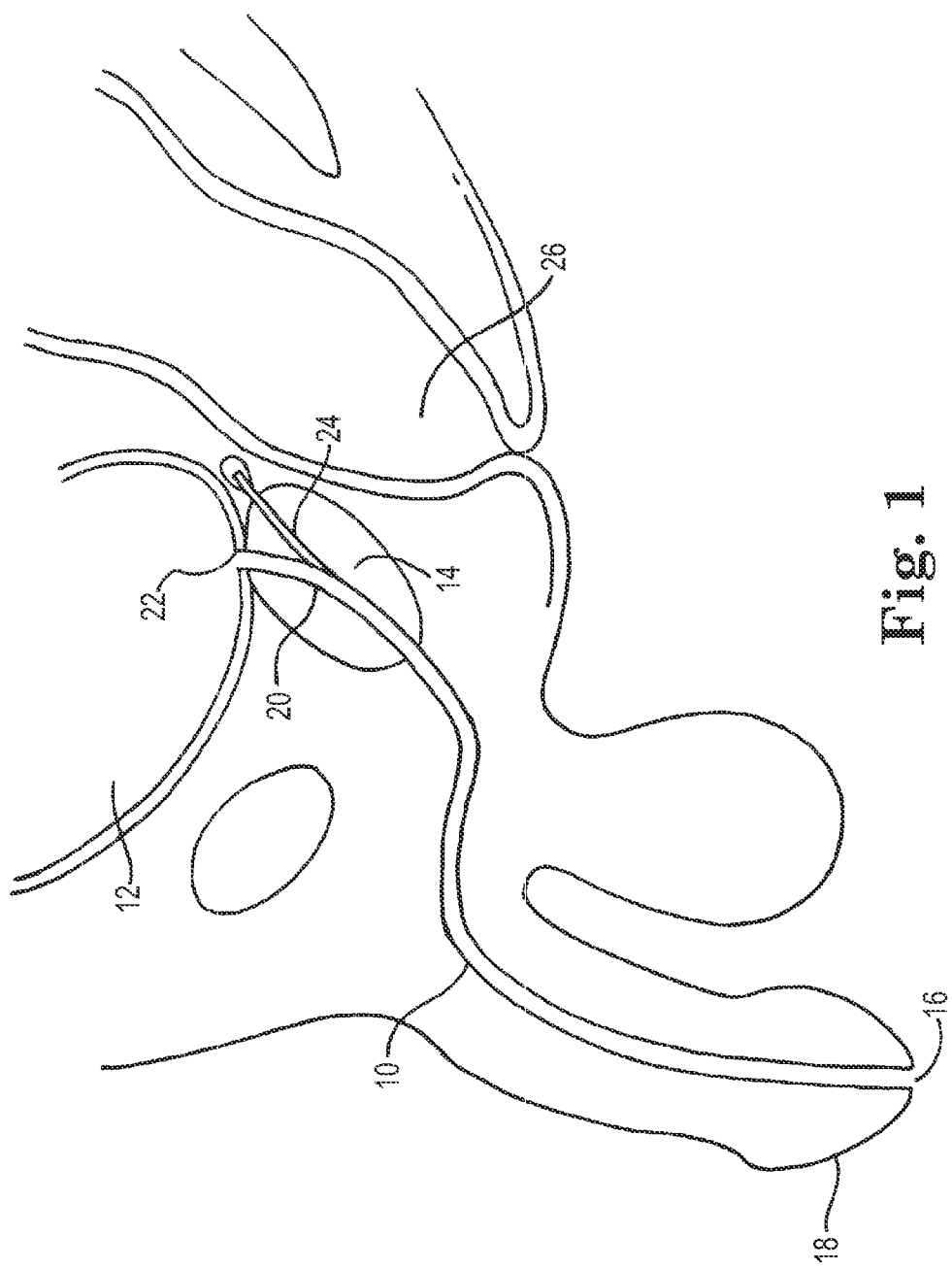
FIG. 1 is a vertical sectional view of a male pelvic region showing the urinary organs affected by benign prostatic hyperplasia.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Embodiments of the present invention are directed to a device insertable into a body for treating tissue and which includes a cooled antenna. In some embodiments, the device comprises a microwave delivery catheter that provides generally direct cooling of a microwave antenna within the catheter. In one embodiment, a catheter shaft includes an array of cooling lumens and an antenna-and-cooling lumen through which the microwave antenna extends. The microwave antenna and the antenna-and-cooling lumen are sized to permit cooling fluid to flow through the antenna-and-cooling lumen around and by the microwave antenna. Accordingly, the antenna-and-cooling lumen simultaneously houses the antenna and provides generally direct cooling for the antenna in addition to cooling provided via the other respective cooling lumens.

In one aspect, this direct cooling of antenna better protects the internal structures of the catheter shaft that generally surrounds the antenna, while providing substantially greater cooling in the surrounding non-prostatic tissues such as the urethra. In addition, the flow of the actively cooled fluid immediately adjacent the antenna helps to reduce "hot spots" in the surrounding tissues because the cooling fluid flowing immediately adjacent the antenna provides a generally uniform and predictable dielectric environment surrounding the antenna.

In addition, this generally direct cooling within the near-field of the microwave energy field generated by the antenna reduces variability in tuning the antenna. In particular, the cooling fluid passes immediately adjacent the antenna, which is covered via a more precisely controlled thickness of dielectric material. This arrangement dominates the dielectric environment surrounding the antenna within catheter shaft, which in turn effectively reduces the relative impact of other structures (e.g. manufacturing variability in walls of catheter shaft) within the dielectric environment and that would otherwise more dramatically affect tuning of the antenna from catheter to catheter. Embodiments of the present invention provide for the antenna extending through the antenna-and-cooling lumen without any adhesive surrounding the antenna. This arrangement eliminates potential voids and/or varying thicknesses typically associated with adhesives surrounding an antenna, thereby further contributing to a consistent, predictable dielectric environment, which in turn further reduces variability in tuning the antenna from catheter to catheter.

In another aspect, in some embodiments the antenna is covered with a single, generally thin-walled sleeve having a generally uniform thickness, which further contributes to a more uniform dielectric environment. In some embodiments, this sleeve also covers a pair of silicone tubes positioned as opposite ends of the antenna such that the combination of the sleeve over the silicone tube sealingly isolates the antenna from fluids.

In another aspect, because embodiments of the present invention produce a substantially more consistent dielectric environment for the antenna within the catheter shaft, it becomes more feasible to perform power testing or tuning of the antenna prior to installation of the antenna within a catheter shaft. This initial testing reduces later discovery of a poorly performing antenna after installation within a catheter shaft.

In addition, embodiments of the present invention also recognize that the specific absorption rate (SAR) for a dipole antenna can be balanced by changing a thickness of a near field material, such as the sleeve that covers the coils of the antenna. Accordingly, this ability allows the antenna to be configured with a single pitch winding of its coils, rather than multiple pitch windings, thus saving time and money in manufacturing because the pitch no longer need be used to control balance of the SAR field. This arrangement also ameliorates the prior need to identify an optimal transition point at which the coil windings begin a different pitch. Moreover, in some embodiments that employ a relatively thinner dielectric layer between the antenna and coolant, a greater pitch coil is usable, thereby permitting a cost-saving construction in which a shorter length of coil is used to form the antenna, if desired.

Moreover, a thickness of the sleeve covering is selectable to match a length of the antenna to achieve the desired SAR field and/or to achieve a uniform or intentionally asymmetric SAR field. For example, a generally thinner sleeve covering tends to produce greater SAR components on a driven element (relative to a non-driven element) of a dipole antenna while a generally thicker sleeve covering tends to produce greater SAR components on a non-driven element (relative to a driven element) of a dipole antenna. By accounting for factors such as a length of the antenna coil, its pitch, and the dielectric properties of the sleeve covering, one can select a thickness of the sleeve covering to produce a desired SAR field for a given antenna. Similarly, selection of the thickness of the sleeve covering, while accounting for other factors (e.g. pitch, tap point location, matching capacitor value) of the antenna, allows one to achieve a desired resonant frequency.

Embodiments of the present invention also accommodate manufacturing variances in an outer diameter of the antenna or an inner diameter of the antenna-and-cooling lumen. In particular, when a generally tight fit exists of the antenna within the antenna-and-cooling lumen, the generally helical arrangement of the coil windings defines a generally helical flow path for the cooling fluid between the adjacent coil windings of the antenna. Accordingly, via the helical groove between adjacent windings of the antenna, fluid can flow through the antenna-and-cooling lumen from one end to another end of the antenna portion of catheter even when the fluid cannot flow directly axially through the antenna-and-cooling lumen.

Embodiments of the present invention also prevent longitudinal migration or movement of the antenna relative to a retention or location balloon, thereby ensuring a predicted location of the antenna relative to the prostatic tissue to be thermally treated. In particular, in one embodiment, the antenna assembly includes an anchor portion extending distally from the antenna and configured to be secured relative to a distal portion of the catheter shaft. The anchor portion exhibits significant tensile strength to ensure integrity of the anchoring mechanism. The anchor portion is sized and shaped to permit flow of actively cooled fluid to pass by the antenna within the antenna-and-cooling lumen and to communicate with other cooling lumens of the catheter shaft. Finally, by securing the antenna in this manner, more flexibility in the treatment area of the catheter is afforded when maneuvering the catheter and during treatment, thus increasing patient comfort while also allowing efficient heat transfer via more uniform pressure on a surrounding urethral tissue.

These embodiments, and other embodiments, of the present invention are described and illustrated in association with FIGS. 1-25.

FIG. 1 is a vertical sectional view of a male pelvic region showing the effect benign prostatic hyperplasia (BPH) has on the urinary organs. Urethra 10 is a duct leading from bladder 12, through prostate 14 and out orifice 16 of penis end 18. Benign tumorous tissue growth within prostate 14 around urethra 10 causes constriction 20 of urethra 10, which interrupts the flow of urine from bladder 12 to orifice 16. The tumorous tissue of prostate 14 which encroaches urethra 10 and causes constriction 20 can be effectively removed by heating and necrosing the encroaching tumorous tissue. Ideally, with the present invention, a selected volume of tissue of prostate 14 can be necrosed while preserving the tissue of urethra 10 and adjacent tissue such as ejaculatory duct 24 and rectum 26. This is achieved by microwave antenna-carrying catheter 28, according to embodiments of the present invention, which is shown in FIGS. 2-25.

Catheter System

Figure 2:
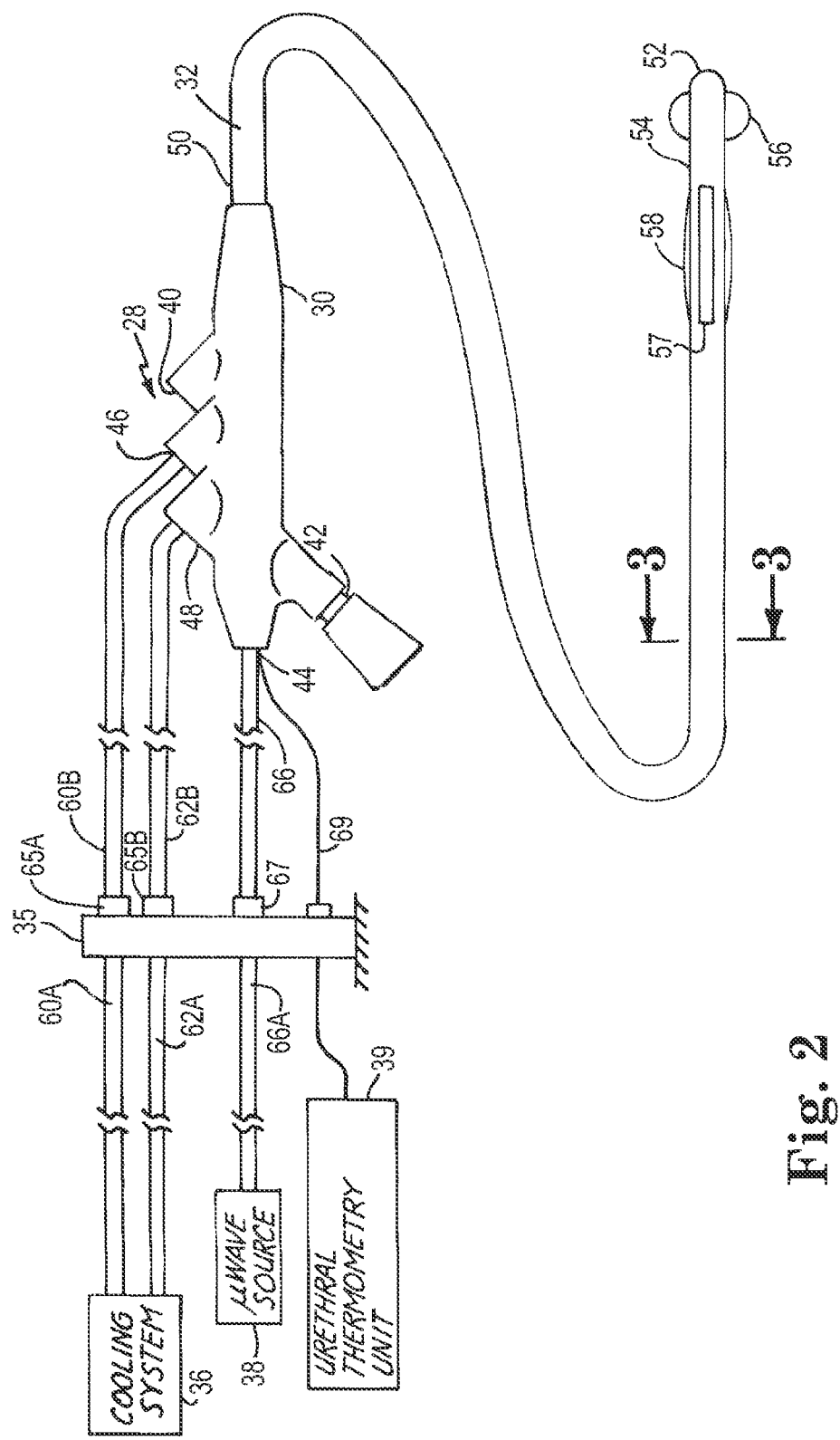
FIG. 2 is a diagram illustrating a thermal therapy catheter, according to one embodiment of the present invention.

FIG. 2 is a diagram illustrating a thermal therapy catheter system, according to an embodiment of the present invention. This system comprises catheter 28 and generally includes multi-port handle 30, multi-lumen shaft 32, connection manifold 35, cooling system 36, microwave generating source 38 and thermometry unit 39. Multi-port handle 30 includes inflation port 40, urine drainage port 42, microwave antenna port 44 (which also receives a temperature sensing fiber), cooling fluid intake port 46 and cooling fluid exit port 48. Ports 40-48 communicate with corresponding lumens within shaft 32. Handle 30 is preferably constructed as a two-piece snap-fit shell, composed of a thermoplastic elastomer or a similar material.

Shaft 32 is connected to handle 30 at shaft proximal end 50, and extends to tip 52 at distal end 54. Shaft 32 is a multi-lumen, Foley-type urethral catheter, with inflatable retention balloon 56 at distal end 54. Shaft 32, which has an outer diameter of about 18 French (6 millimeters (mm)), is generally circular in cross-section, and is both long enough and flexible enough to permit insertion of proximal shaft end 54 through urethra 10 into bladder 12 (FIG. 1), where retention balloon 56 is inflated and seated against the bladder neck to secure the catheter in place. This enables precise location of microwave antenna 57 with respect to prostate tissue. In a preferred embodiment, catheter shaft 32 is extruded from a thermoplastic elastomer.

Multi-lobe balloon 58 is attached to the outer surface of shaft 32 near distal end 54, preferably by thermal welding or a comparable attachment technique such as adhesive bonding, at one or more points on the outer surface of shaft 32 around antenna 57. Multi-lobe balloon 58 is preferably formed of a thermoplastic film wrapped around shaft 32, such as a cross-linked polyurethane blown film in an exemplary embodiment. The construction and operation of multi-lobe balloon 58 is described in more detail below. In some embodiments, the multi-lobe balloon 58 is replaced with a single balloon structure lacking separate lobes.

Cooling system 36 provides cooling fluid in feed line 60A, which is coupled through manifold 35 to feed line 60B and on through port 46 of handle 30 for communication with an interior lumen of catheter shaft 32. The cooling fluid returns from the interior of catheter shaft 32 through port 48 of handle 30, into return line 62B through manifold 35 to return line 62A and back to cooling system 36 for re-chilling and recirculation. Cooling fluid feed line 60B and return line 62B are provided with conventional fittings 65A and 65B, respectively, which permits catheter 28 to be easily disconnected from cooling system 36. In an exemplary embodiment, the cooling fluid is deionized or sterile water, chilled to an appropriate temperature for effective tissue cooling in operation of catheter 28.

Microwave generating source 38 provides microwave energy to connection cable 66A, which is coupled through manifold 35 to coaxial cable 66. Coaxial cable 66 is provided with conventional connector 67 to permit coaxial cable 66 to be easily disconnected from microwave source 38. Coaxial cable 66 extends through port 44 of handle 30 into an internal lumen of catheter shaft 32 that extends to distal end 54. In some embodiments, microwave generating source 38 produces up to about 100 watts of electrical power in a frequency range of 902-928 MHz, within the FCC-ISM standard range of frequencies.

Urethral thermometry unit 39 is operatively connected to temperature sensing fiber 69, which extends through manifold 35 into port 44 of handle 30 and on to an internal lumen of catheter shaft 32 that extends to distal end 54. Signals representative of urethral temperature are communicated via temperature sensing fiber 69 and are interpreted and processed by urethral thermometry unit 39. In some embodiments, temperature sensing fiber 69 is encased in a Kevlar tube, attached to fiber 69 with sufficient slack between tip 52 and handle 30 so that pulling on the exposed portion of the tube outside handle 30 will not break fiber 69.

Figure 3:
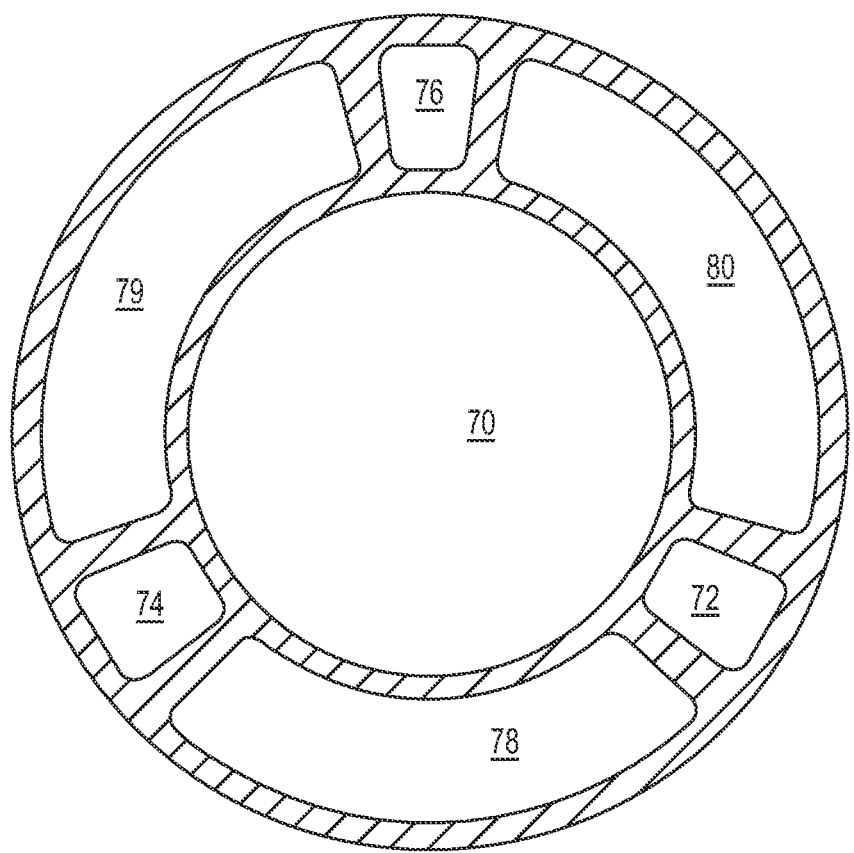
FIG. 3 is a cross-sectional view, as taken along line 3-3 of FIG. 2, of the thermal therapy catheter, according to one embodiment of the present invention.

FIG. 3 is a sectional view of catheter shaft 32 taken along line 3-3 of FIG. 2, for illustration of the interior lumens of shaft 32. Shaft 32 includes antenna-and-cooling lumen 70, temperature sensing fiber lumen 72, urine drainage lumen 74, balloon inflation lumen 76, and cooling lumens 78, 79 and 80. Lumens 70, 72, 74, 76, 78, 79 and 80 generally extend from proximal shaft end 50 to distal shaft end 54, and are formed by walls within catheter shaft 32 that have a substantially uniform thickness throughout the cross-section of shaft 32, the catheter wall thickness being about 0.008 inches in an exemplary embodiment. Although coaxial cable 66 and fiber 69 are contained in shaft 32, they are omitted from FIG. 2 in order to more clearly show the relationships between the interior lumens of catheter shaft 32.

FIGS. 4A and 4B are cross-sectional views of catheter shaft 32 in a region including multi-lobe balloon 58 and retention balloon 56, respectively. Coaxial cable 66 is positioned within antenna-and-cooling lumen 70 and extends along the length of shaft 32. Formed on the end of coaxial cable 66 is microwave antenna 57, which is surrounded by multi-lobe balloon 58. In some embodiments, microwave antenna-and-cooling lumen 70 is located eccentric to the longitudinal axis of shaft 32, nearer first side 82 of shaft 32 than second side 84 of shaft 32. In one embodiment, the center of antenna-and-cooling lumen 70 is offset from the center of shaft 32 towards first side 82 of shaft 32 by 0.007 inches. Alternatively, antenna-and-cooling lumen 70 maybe centered within catheter shaft 32.

As shown in FIG. 4B, in one embodiment, antenna-and-cooling lumen 70 is sealed at a distal end by plugs 70A and 70B, forming cavity 86 therebetween. As will be later described in more detail, in other embodiments, the distal portion of antenna-and-cooling lumen 70 has other configurations depending on the particular defined fluid flow path of the various embodiments of the present invention. At its proximal end, microwave antenna-and-cooling lumen 70 communicates with microwave antenna port 44 of handle 30 (FIG. 2). Microwave antenna 57 is permanently positioned within antenna-and-cooling lumen 70 adjacent distal end 54 of shaft 32 near retention balloon 56, and is held in place via anchoring of its distal end relative to a distal end of catheter shaft 32. As further shown in FIGS. 4A-4B, in one embodiment a gap 87 extends between antenna 57 and the wall defining antenna-and-cooling lumen. This gap 87 facilitates flow of cooling fluid through antenna-and-cooling lumen 70 to accentuate cooling near antenna 57. It will be understood that the coil windings of antenna 57 would have a sleeve covering, which is not shown in FIGS. 4A-4B for illustrative purposes. The relationship between antenna 57 and antenna-and-cooling lumen 70 will be further described later in association with at least FIGS. 6-19B.

In general terms, antenna 57 is positioned within antenna-and-cooling lumen 70 so as to be generally situated adjacent the diseased tissue of prostate 14 when shaft 32 is properly positioned in urethra 10. Antenna 57 includes wound coils carried at the distal end of coaxial cable 66, which carries microwave energy generated by microwave generating source 38 (FIG. 2). In some embodiments, microwave antenna 57 is an impedance-matched antenna implemented in the manner generally disclosed in U.S. Pat. No. 5,300,099 entitled GAMMA MATCHED HELICAL DIPOLE MICROWAVE ANTENNA, which is hereby incorporated by reference. In some embodiments, antenna 57 has a relatively large radial cross-section, about 0.131 inches in an exemplary embodiment, since a larger antenna radius can be constructed with larger coaxial cable that results in lower transmission line losses and also provides greater column stiffness to facilitate insertion of shaft 32 into urethra 10. More specifically, in the embodiment where microwave antenna-and-cooling lumen 70 is located nearer first side 82 of shaft 32 than second side 84 of shaft 32, the orientation of shaft 32 in urethra 10 must be controlled to achieve the desired preferential heating pattern (with more heating on the side to which the antenna is offset, due to the shorter distance between the antenna and tissue on that side). This embodiment is employed where it is desirable to direct less heat in the portion of the prostate toward the rectum than in other portions of the prostate away from the rectum, due to the potential for thermal damage to the rectum (although in other embodiments, a control system may be employed to circumvent this possibility and prevent thermal damage to the rectum). Thus, the antenna assembly is designed to effectively transmit 100% of the torque applied to handle 30 on to the tip of shaft 32 at distal end 54, through porous heat-shrink tubing 85 bonding coaxial cable 66 to the wall of antenna-and-cooling lumen 70 in a region near handle 30 (not shown) and in a region near (but proximal to) antenna 57 (shown in FIG. 4A). In other words, if handle 30 is rotated 20 degrees, the tip of shaft 32 at distal end 54 also rotates 20 degrees. When antenna 57 is energized by microwave generating source 38, antenna 57 emits electromagnetic energy which causes heating of tissue within prostate 14.

In an exemplary embodiment of the thermal therapy catheter of the present invention, a special tip may be used at distal end 54 of catheter shaft 32 as is generally known in the art.

With further reference to FIGS. 4A-4B, in the vicinity of multi-lobe balloon 58, tube 81 is positioned and secured on the outer surface of shaft 32 at a point where the material of balloon 58 has been attached to shaft 32. Tube 81 is a fluid-free tube with a closed distal end and a proximal end which communicates through the wall of shaft 32 with temperature sensing fiber lumen 72. Tube 81 has a length that approximates the length of multi-lobe balloon 58. Temperature sensing fiber lumen 72, temperature sensing fiber tube 81 and the channel therebetween are sized to permit insertion of temperature sensing fiber 69 to monitor the temperature of tissue surrounding shaft 32 when it is inserted into urethra 10, for interpretation and processing by urethral thermometry unit 39 (FIG. 2).

Balloon inflation lumen 76 extends along the length of catheter shaft 32 and communicates through aperture 88 with the interior of retention balloon 56. Inflation fluid supplied under dynamic pressure through inflation port 40 of handle 30 (FIG. 2) to balloon inflation lumen 76 inflates retention balloon 56 through aperture 88 when catheter 28 is properly positioned in urethra 10, with retention balloon 56 positioned in bladder 12.

Cooling lumen 78 extends along the length of catheter shaft 32, providing a path for the flow of cooling fluid therethrough. Plug 78F is positioned in cooling lumen 78 adjacent to a proximal end of multi-lobe balloon 58 to cause a particular fluid flow path through cooling lumen 78 and multi-lobe balloon 58. The fluid flow path provided according to embodiments of the present invention is described in more detail below.

In general terms, FIGS. 5-10B illustrate a defined fluid flow path through the various cooling lumens 78-80, antenna-and-cooling lumen 70, and lobes 58A-58C of balloon 58. This fluid flow path includes directing cooled fluid to flow through antenna-and-cooling lumen 70 immediately adjacent antenna 57 to accentuate cooling of catheter 28 and nearby tissues during application of heat via antenna 57 when applying thermal therapy to prostatic tissues.

Figure 7:
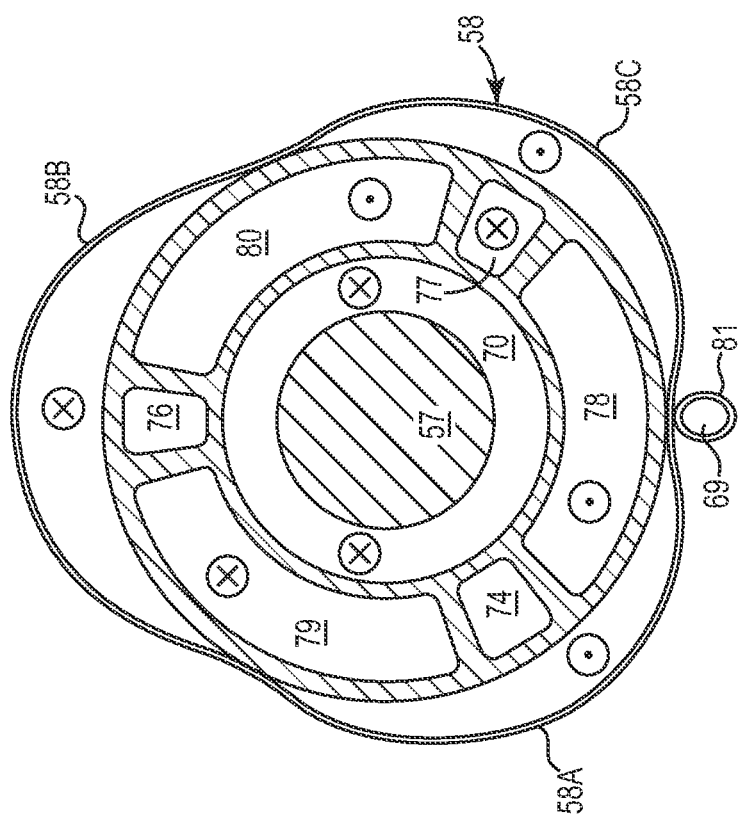
FIG. 7 is a cross-sectional view, as taken along line 7-7 of FIG. 6, of the thermal therapy catheter, according to one embodiment of the present invention.

With reference to FIG. 7, urine drainage lumen 74 is positioned adjacent antenna-and-cooling lumen 70, between antenna-and-cooling lumen 70 and lobe 58A of multi-lobe balloon 58. In some embodiments, urine drainage lumen 74 has a generally trapezoidal cross-section, and together with the catheter walls on either side between cooling lumens 78 and 79 has an included angle of about 30.5 degrees. Urine drainage lumen 74 communicates with urine drainage port 42 of handle 30 (FIG. 2) at proximal end 50 of shaft 32 and with the interior of the bladder at the distal end of catheter shaft 32, and defines a drainage path for urine when catheter shaft 32 is inserted through the urethra into the bladder. Drainage of urine from bladder 12 is necessary due to frequent bladder spasms which occur during transurethral thermal therapy. Again, as mentioned above, in an exemplary embodiment a special tip design maybe used with catheter 28, as is generally known in the art.

As shown in at least FIG. 7, balloon inflation lumen 76 is located adjacent antenna-and-cooling lumen 70, between antenna-and-cooling lumen 70 and lobe 58B of multi-lobe balloon 58. In some embodiments, balloon inflation lumen 76 has a generally trapezoidal cross-section, and together with the catheter walls on either size between cooling lumens 79 and 80 has an included angle of about 29 degrees. Balloon inflation lumen 76 communicates between inflation port 40 of handle 30 (FIG. 2) and the interior of retention balloon to allow for inflation and deflation of balloon 56 (FIG. 4B).

As further shown in FIG. 7, cooling lumens 78, 79 and 80 are positioned circumjacent to antenna-and-cooling lumen 70. In this arrangement, cooling lumen 78 is located generally between antenna-and-cooling lumen 70 and temperature sensing fiber tube 81 (between lobes 58A and 58C of multi-lobe balloon 58). At the same time, cooling lumen 79 is located generally between antenna-and-cooling lumen 70 and lobes 58A and 58B of multi-lobe balloon 58. In addition, cooling lumen 80 is located generally between antenna-and-cooling lumen 70 and lobes 58B and 58C of multi-lobe balloon 58. Cooling lumens 78, 79 and 80 each have a generally arcuate cross-section, and extend along the length of shaft 32. Cooling lumens 78, 79 and 80 allow for the circulation of fluid around antenna 57 located in antenna-and-cooling lumen 70, and also provide part of a fluid pathway enabling fluid to flow through antenna-and-cooling lumen 70 via gap 87 (FIGS. 4A, 4B) to directly surround and cool microwave antenna 57 with circulating cooling fluid. Fluid contained within cooling lumens 78, 79 and 80, as well as within antenna-and-cooling lumen 70, absorbs a portion of the microwave energy emitted by microwave antenna 57 to control the volume of prostatic tissue in a selected direction that is heated above 45 degrees Celsius for a time sufficient to necrose the tissue. Fluid within cooling lumens 78, 79 and 80, as well as within antenna-and-cooling lumen 70, also absorbs a portion of the heat energy generated by microwave energy from adjacent tissues via thermal conduction.

Figure 5:
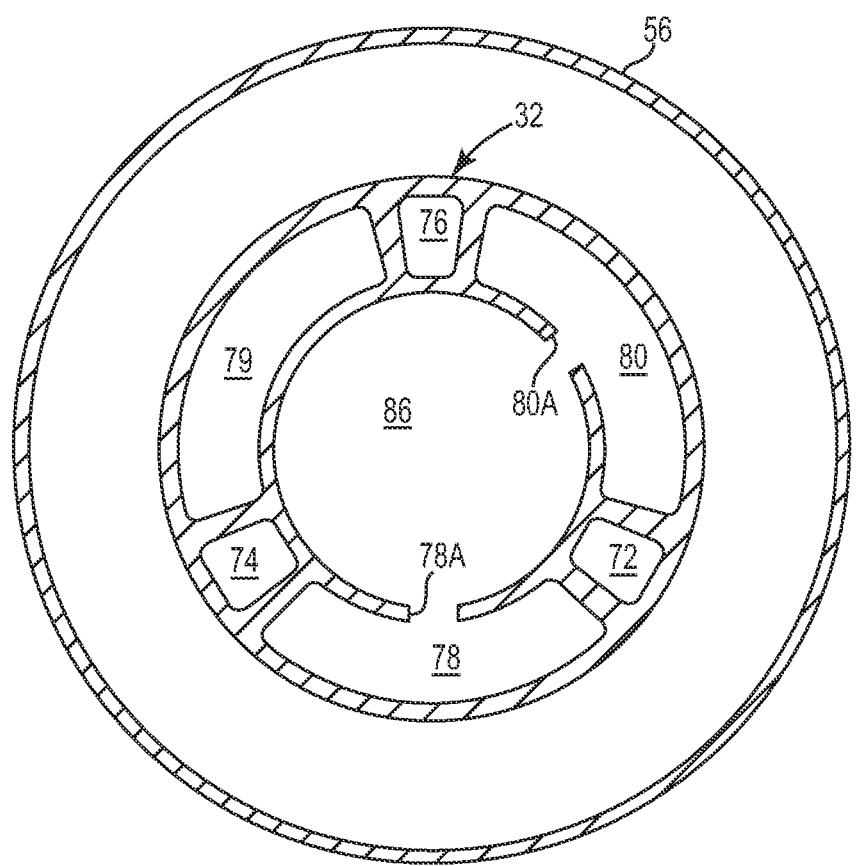
FIG. 5 is a cross-sectional view, as taken along line 5-5 of FIG. 4B, of the thermal therapy catheter, according to one embodiment of the present invention.

FIG. 5 is a cross-sectional view of catheter shaft 32 taken along line 5-5 of FIG. 4B, and generally illustrates a relationship of the respective lumens of catheter shaft 32 and lobes in the vicinity of retention balloon 56. As shown in FIG. 5, at one location along their length, cooling lumens 78 and 80 include apertures 78A and 80A, respectively, for allowing fluid communication therebetween via cavity 86 (FIG. 4B) in antenna-and-cooling lumen 70. In one embodiment, cooling lumens 78, 79 and 80 each have an included angle of about 90 degrees.

Figure 6:
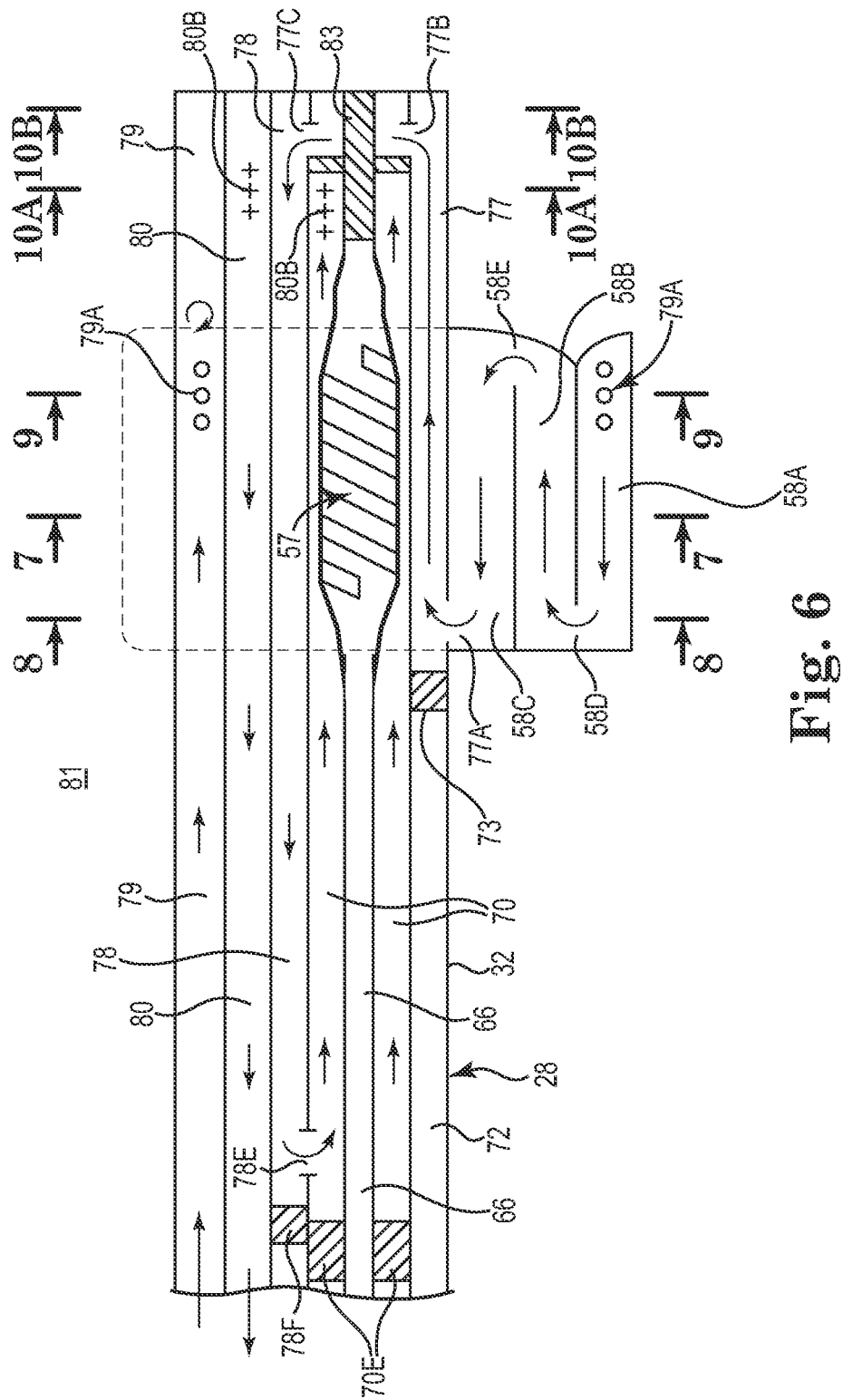
FIG. 6 is a diagram schematically illustrating a defined fluid flow path of a thermal therapy catheter, according to one embodiment of the present invention.

FIG. 6 is a diagram 81 that schematically illustrates a fluid flow path for catheter shaft 32 in the vicinity of cooling balloon 58 as cooling fluid passes through the respective lumens of catheter shaft 32 and respective lobes of balloon 58. In FIG. 6, the respective lumens and lobes are laid out in a side-by-side manner and include directional arrows that indicate a direction of fluid flow through each of the respective lumens and lobes. For the purpose of illustration, lumens 70-80 of catheter shaft 32 and multi-lobe balloon 58 is shown in FIG. 6 as being "flattened out" in two dimensions. However, it should be understood that multi-lobe balloon 58 is wrapped around catheter shaft 32 in a final assembly in embodiments of the present invention, as shown in the sectional views of FIGS. 5 and 6-10B. For example, while in actuality the lobes 58A-58C surround the catheter shaft 32 in a generally circular pattern, in FIG. 6, the lobes 58A-58C are illustrated in a side-by-side manner to display the lobes 58A-58C simultaneously with display of the respective lumens 70-78 of catheter shaft 32.

Figure 8:
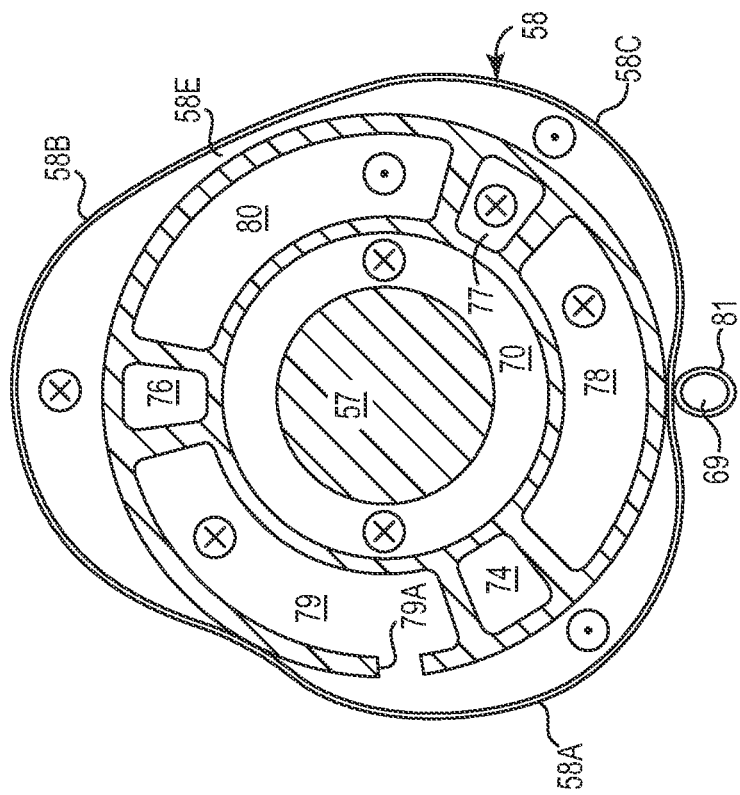
FIG. 8 is a cross-sectional view, as taken along line 8-8 of FIG. 6, of the thermal therapy catheter, according to one embodiment of the present invention.
Figure 9:
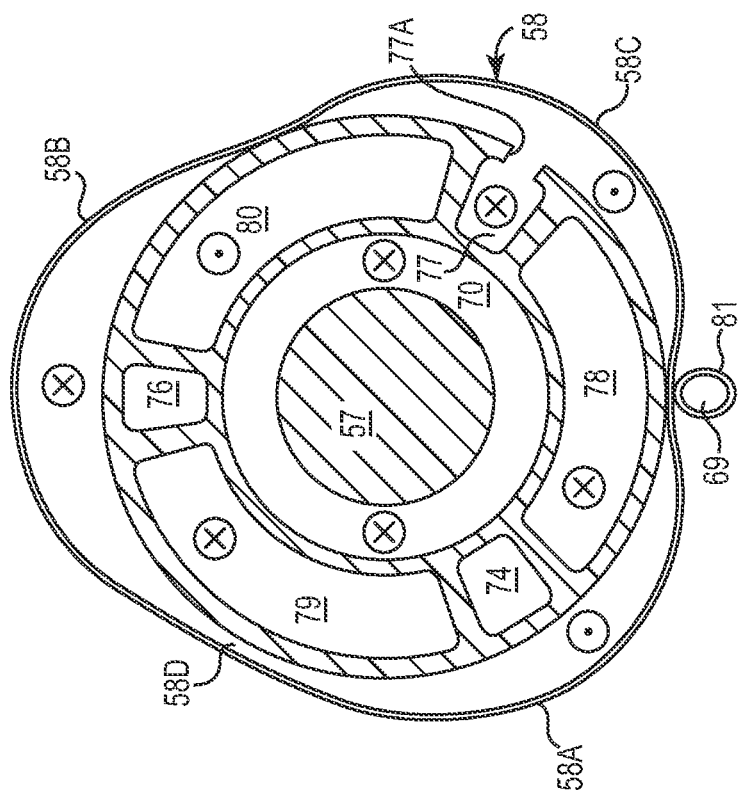
FIG. 9 is a cross-sectional view, as taken along line 9-9 of FIG. 6, of the thermal therapy catheter, according to one embodiment of the present invention.

In addition, the cross-sectional views of FIGS. 7-9 further aid in an understanding of the fluid flow path within the lumens 70-78 of catheter shaft 32 and lobes 58A-58C of balloon 58. FIG. 7 is a cross-sectional view of catheter shaft 32 taken along line 7-7 of FIG. 6. FIG. 8 is a cross-sectional view of catheter shaft 32 taken along line 8-8 of FIG. 4A, which also corresponds to section 8-8 of diagram 81 of catheter in FIG. 6. FIG. 9 is a cross-sectional view of catheter shaft 32 taken along line 9-9 of FIG. 4A, which also corresponds to section 9-9 of the diagram 81 of catheter in FIG. 6. As seen in the cross-sectional views, fluid flowing distally or toward antenna 57 of catheter 28 is represented as an "x" inside a circle, while fluid flowing proximally or away from antenna 57 is represented as a dot inside a circle.

While FIG. 4A and FIG. 4B illustrate multi-lobe balloon 58 in its deflated state, for insertion of catheter 28 into urethra 10, FIGS. 6-10B illustrate multi-lobe balloon 58 in its inflated state, for operating to cool the wall of urethra 10 when microwave antenna 57 is energized.

Fluid Flow Path

With this in mind, in general terms, cooling lumens 70, 78, 79 and 80 cooperate with cooling system 36 via ports 46 and 48 of handle 30 (FIG. 2) to provide a path for selectively controlled flow of fluid through cooling lumens 70, 78, 79 and 80 and through lobes 58A, 58B and 58C of multi-lobe balloon 58 during a treatment session. Cooling lumens 70, 78, 79 and 80 and multi-lobe balloon 58 are designed to provide a path for the flow of fluid therethrough, providing advantageous cooling performance. In one embodiment, the fluid flows in a serpentine pattern through the respective lobes 58A, 58B, and 58C, as shown in FIG. 6.

In this arrangement, cooling fluid flows from cooling system 36 to cooling fluid feed line 60B and on through port 46 of handle 30 (FIG. 2) into cooling lumen 79, which serves as a fluid intake lumen. As shown in FIG. 6, the cooling fluid flows under dynamic fluid pressure in cooling lumen 79 toward distal end 54 of shaft 32, and exits cooling lumen 79 via aperture 79A to enter lobe 58A of balloon 58 (see FIG. 9) to begin a flow path through the lobes of balloon 58.

In particular, cooling fluid enters lobe 58A from lumen 79 (via aperture 79A, which is represented by a series of circles in FIG. 6) as shown in FIG. 9 and flows under dynamic pressure through the respective lobes 58A-58C of balloon 58 in the serpentine pattern (indicated by the arrows in FIG. 6) from lobe 58A through narrow channel 58D to lobe 58B, and through narrow channel 58E to lobe 58C. As illustrated in both FIGS. 6 and 8, the cooling fluid exits lobe 58C of balloon 58 through aperture 77A into distal portion 77 of fiber lumen 72 of catheter shaft 32. In one aspect, distal portion 77 of fiber lumen 72 acts as an additional or auxiliary cooling lumen extending parallel to and adjacent the antenna 57 and antenna-and-cooling lumen 70. In one embodiment, the auxiliary lumen 77 is formed via plug 73 which isolates distal portion 77 from the proximal portion (denoted as lumen 72) with plug 73 being located proximal to balloon 58.

Figure 10B:
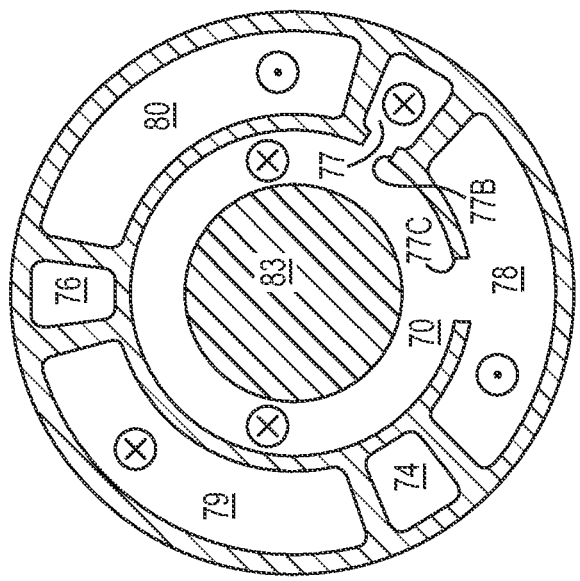
FIG. 10B is a cross-sectional view, as taken along line 10B-10B of FIG. 6, of the thermal therapy catheter, according to one embodiment of the present invention.
Figure 10A:
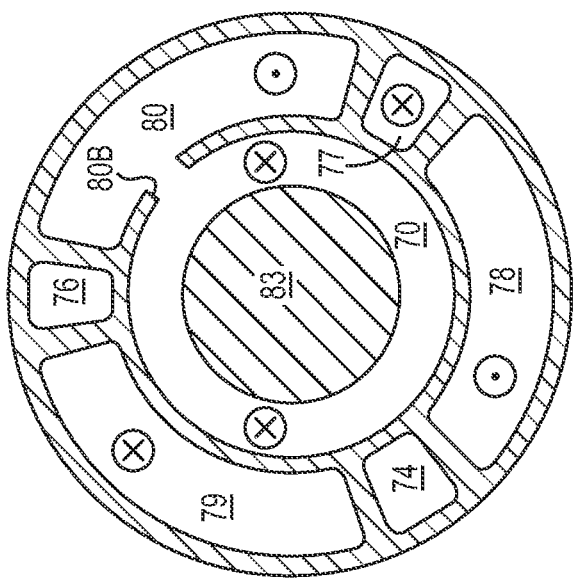
FIG. 10A is a cross-sectional view, as taken along line 10A-10A of FIG. 6, of the thermal therapy catheter, according to one embodiment of the present invention.

In addition, as illustrated in both FIGS. 6 and 10B, this distal portion 77 of fiber lumen 72 provides a passageway to fluidly communicate with cooling lumen 78 via apertures 77B and 77C, such that fluid flows from balloon lobe 58C, via distal portion 77, to cooling lumen 78. In one aspect, as fluid flows from distal portion 77 to lumen 78, the fluid flows around a distal anchor portion 83 of catheter 28, as illustrated in FIG. 6.

As shown in FIG. 6, from aperture 77C, cooling fluid flows distally through cooling lumen 78 toward proximal end 50 of shaft 32 until the cooling fluid exits cooling lumen 78 through aperture 78E into antenna-and-cooling lumen 70 for travel distally back toward antenna 57. In one embodiment, a plug or other barrier 78F is located proximal to aperture 78E and causes the cooling fluid to exit lumen 78 into lumen 70. This arrangement directs cooling fluid through antenna-and-cooling lumen 70 to surroundingly flow by and around antenna 57 within the antenna-and-cooling lumen 70. In one embodiment, a plug or other barrier 70E is located within antenna-and-cooling lumen 70 proximal to aperture 78E to force fluid to flow toward antenna 57.

With this arrangement, the cooling lumens 78, 79, 80, and auxiliary lumen 77 (defined as the isolated distal portion of fiber lumen 72) are at a minimum generally coextensive with the antenna 57, and preferably extend distally beyond a distal end of the antenna 57 to ensure that cooling surrounds the field generated by antenna 57. Therefore, the cooling lumens 78, 79, 80 (and lumen 77) are at least generally coextensive with antenna-and-cooling lumen 70 along the length of antenna 57 to accentuate the cooling surrounding antenna 57.

In another aspect, it will be understood that the cooling fluid passing through antenna-and-cooling lumen flows beside antenna 57, but external to the metal conductive material defining the coil windings of the antenna 57. Moreover, while the cooling fluid flows in the defined flow path through the various lumens as described above, the cooling fluid is otherwise generally unrestrained by antenna 57 as the fluid passes by the antenna 57 within antenna-and-cooling lumen 70.

Figure 11:
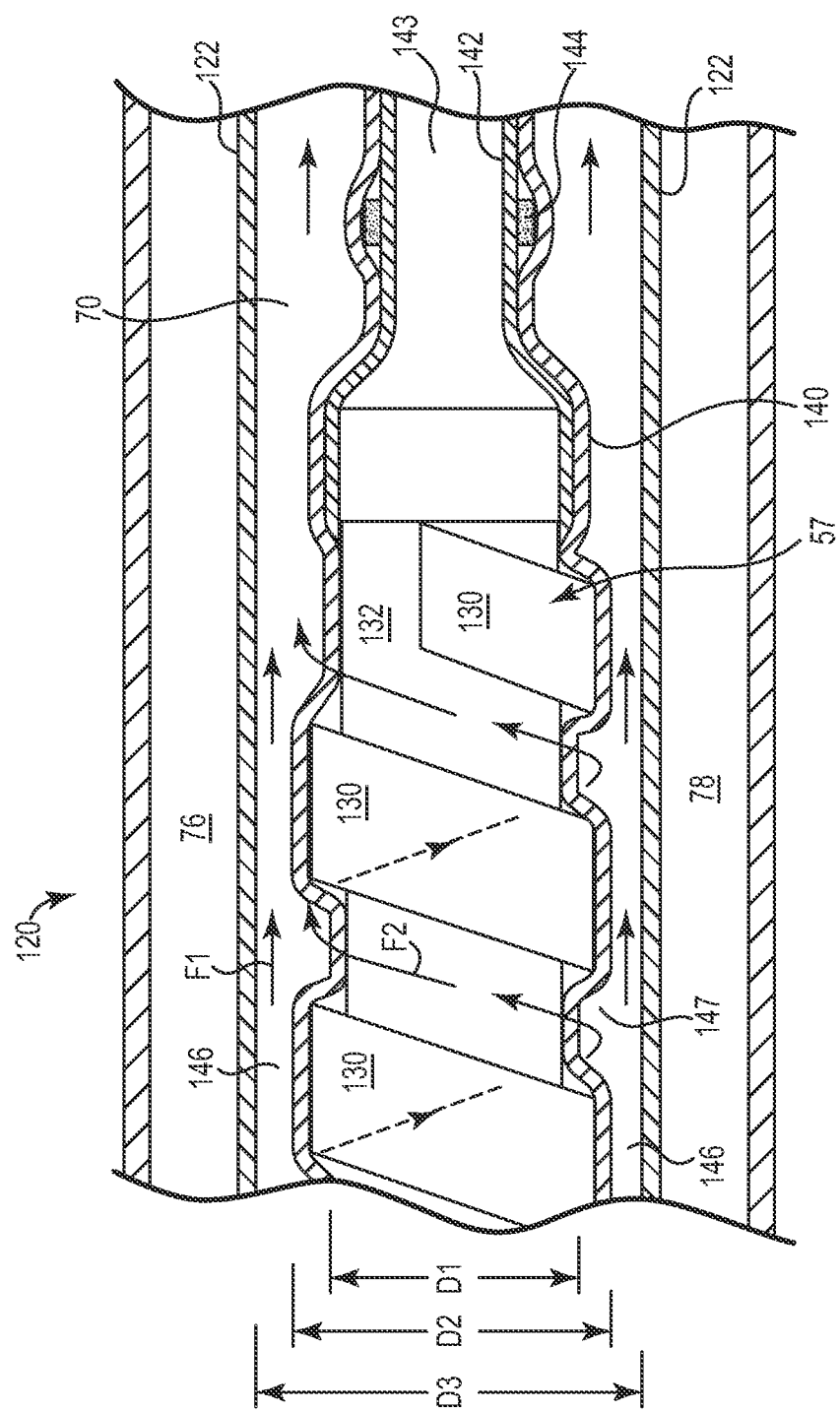
FIG. 11 is an enlarged, partial sectional view of an antenna region of a thermal therapy catheter, according to one embodiment of the present invention.

FIG. 11 is an enlarged, partial sectional view of catheter shaft 32 in the vicinity of balloon 58 and antenna 57 that highlights the manner in which a configuration of antenna 57 accentuates flow of cooling fluid over and by antenna 57 to provide direct cooling action immediately adjacent antenna 57. In particular, as shown in FIG. 11, antenna 57 includes a sleeve cover 140 extending over a core 132 to define a first diameter (D1) and over coil windings 130 to define a second diameter (D2). Particular details regarding the construction of antenna 57 including cover 140 are later described in association with FIGS. 21-25.

As shown in FIG. 11, antenna-and-cooling lumen 70 defines a hollow conduit and has a third diameter (D3) that is larger than either first diameter D1 or second diameter D2. As illustrated in FIG. 11, fluid flows through antenna-and-cooling lumen 70 by antenna 57 in at least a first generally axial flow pattern and a second generally helical flow pattern. The first generally axial flow pattern is represented by directional arrow F1 and passes at least through gaps 146 between each winding 130 and a wall of lumen 70. The second generally helical flow pattern is represented by directional arrow F2 and follows the generally helical pattern over core 132 between adjacent windings 130.

Figure 12:
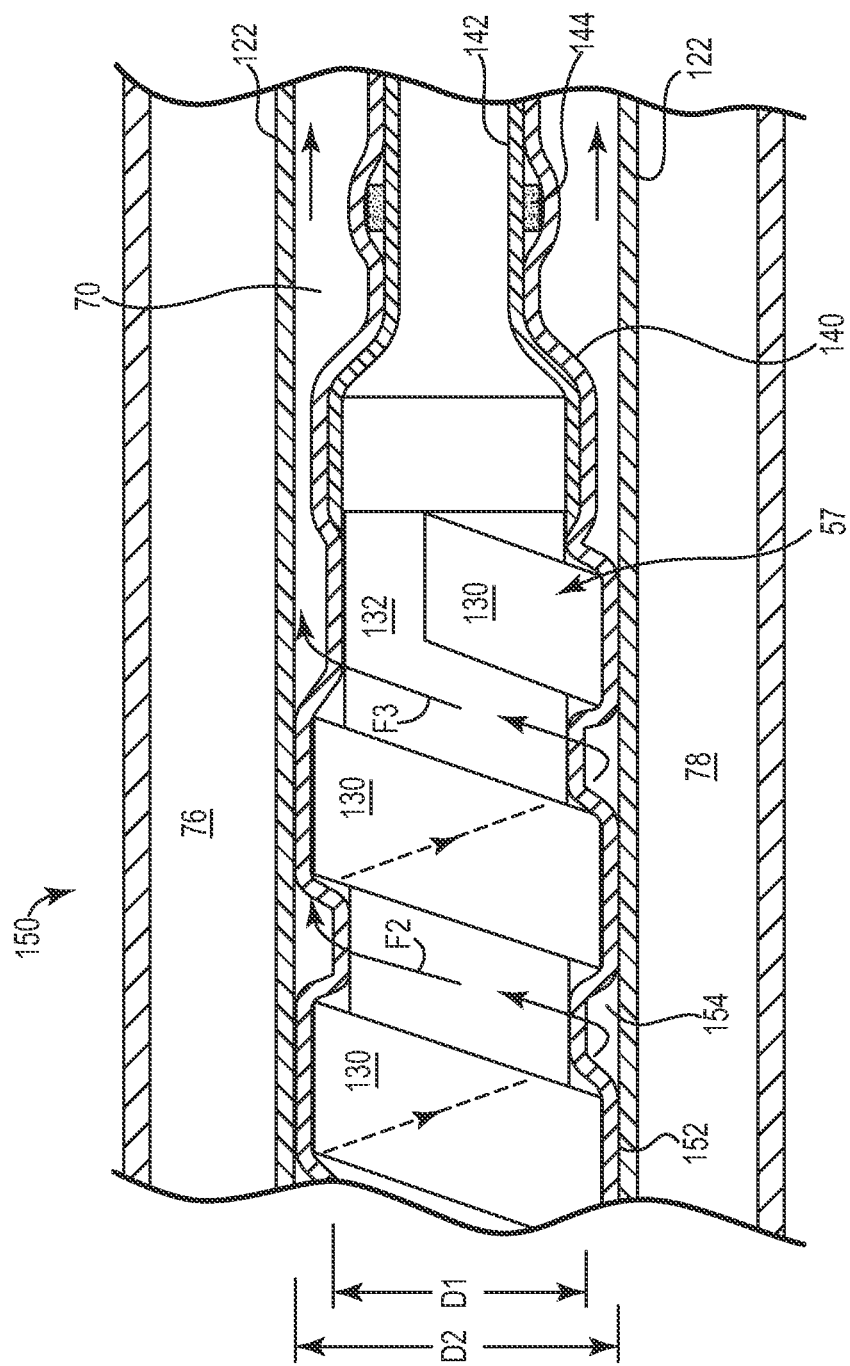
FIG. 12 is an enlarged, partial sectional view of an antenna region of a thermal therapy catheter, according to one embodiment of the present invention.

In some embodiments, antenna 57 is arranged within antenna-and-cooling lumen 70 having a smaller diameter that generally matches second diameter D2 of coil windings, such that little or no gap 146 exists (as represented by contact portion 152) between windings 130 and the wall of the antenna-and-cooling lumen 70, as illustrated in FIG. 12. In this embodiment, cooling fluid flows in a generally helical pattern (as represented by directional arrow F3) through gaps 154 over core 132 and between adjacent windings 130.

By directing the fluid into the immediate proximity of antenna 57 (rather than when cooling fluid is separated from antenna 57 by a wall of a lumen) via antenna-and-cooling lumen 70, as shown in FIG. 6, this catheter 28 provides additional cooling directly at the source of the heat to ameliorate potentially harmful near-heating effects of antenna 57 on the internal, extruded structures of catheter shaft 32 while allowing the antenna 57 to operate at cooler temperatures. Once the cooling fluid passes distally beyond antenna 57, the cooling fluid exits antenna-and-cooling lumen 70 via aperture 80B (represented as a series of +++ symbols) into cooling lumen 80, as illustrated in both FIGS. 6 and 10A. As further shown in FIG. 6, cooling fluid flows through cooling lumen 80, which serves as an exhaust lumen, and exits shaft 32 at proximal end 50 thereof through port 48 of handle 30 (FIG. 2) for later recirculation via cooling system 36.

In addition, the cooling fluid passing through lobes 58A-58C of balloon 58 is also directed to pass adjacent to retention balloon 56 to passively cool the inflation fluid within retention balloon 56, thereby enhancing patient comfort during treatment. In one embodiment, this passive cooling is provided via directing fluid flowing through cooling lumen 79 to exit through an aperture 80A, as shown in FIG. 5, into cavity 86 created in antenna-and-cooling lumen 70 by plugs 70A and 70B, as shown in FIG. 4B. The fluid flows from cavity 86 through aperture 78A into cooling lumen 78, as further shown in FIG. 5, for flow back toward the proximal end of shaft 32.

Accordingly, the overall fluid circulation system described above is operable to circulate cooling fluid throughout cooling lumens 78, 79 and 80, antenna-and-cooling lumen 70, and multi-lobe balloon 58 in a defined fluid flow path, inflating multi-lobe balloon into contact with a wall of the urethra 10.

In one aspect, the fluid flow path provided by embodiments of the present invention ensures that the cooling fluid circulates under sufficient dynamic pressure to inflate multi-lobe balloon 58 to a sufficient diameter to provide consistent wall contact with the urethra 10. In some embodiments, the film forming balloon 58 is formed of a non-distensible material fixable to a size corresponding to the desired inflation diameter of multi-lobe balloon 58. As a result, variations in the dynamic pressure of the cooling fluid flowing through multi-lobe balloon will not affect the inflated diameter of the balloon or the force applied by the balloon to the wall of the urethra.

More complex flow patterns in the lobes of balloon 58 are also contemplated by embodiments of the present invention, which may be realized by heat stamping and thermal welding processes, or alternatively by adhesive bonding processes, to form the appropriate flow pattern. In addition, multi-lobe balloon 58 may be formed with more than the three lobes 58A, 58B and 58C illustrated in FIGS. 6-10B, thereby modifying the fluid flow pattern and inflation characteristics of balloon 58. The actual amount of dynamic fluid flow pressure may be controlled by adjusting a number of parameters, such as the rate at which cooling fluid is pumped from the cooling system, the width of channels 58D and 58E, the size of fluid flow apertures (e.g., 77A, 77B, 77C, 78A, 78B, 78E, 79A, 80A, and 80B), the width of restricted flow areas elsewhere in the fluid flow path, and other parameters that will be apparent to one skilled in the art. In an exemplary embodiment, dynamic fluid pressure is controlled by an adjustable restrictor located in the return fluid flow path proximate to cooling system 36.

In one embodiment, the cooling fluid is deionized or sterile water, chilled to an appropriate temperature so as to maintain the temperature of tissue immediately surrounding catheter shaft 32 at a predetermined value while power is applied to heat diseased prostate tissue. A method of controlling coolant temperature and microwave power to maintain a predetermined tissue temperature is disclosed in U.S. Pat. No. 6,122,551 entitled METHOD OF CONTROLLING THERMAL THERAPY, which is hereby incorporated by reference. The water is pumped at a rate sufficient to provide dynamic pressure to inflate multi-lobe balloon 58 to create an outer balloon diameter of about 24 French (8 mm), with balloon 58 being cross-linked to inflate to this diameter in an exemplary embodiment, thereby ensuring excellent wall contact with the urethra and enhancing the efficiency of the conductive cooling performed by the circulating cooling fluid flowing in multi-lobe balloon 58.

FIGS. 13-15B schematically illustrate a defined fluid flow path of a catheter, according to one embodiment of the present invention. In one embodiment, catheter 128 comprises at least substantially the same general features and attributes as previously described for the catheter 28 in association with FIGS. 1-12, except for providing a different fluid flow path through the respective lumens of the catheter shaft and the respective lobes of the cooling balloon, with like reference numerals denoting like elements.

Figure 13:
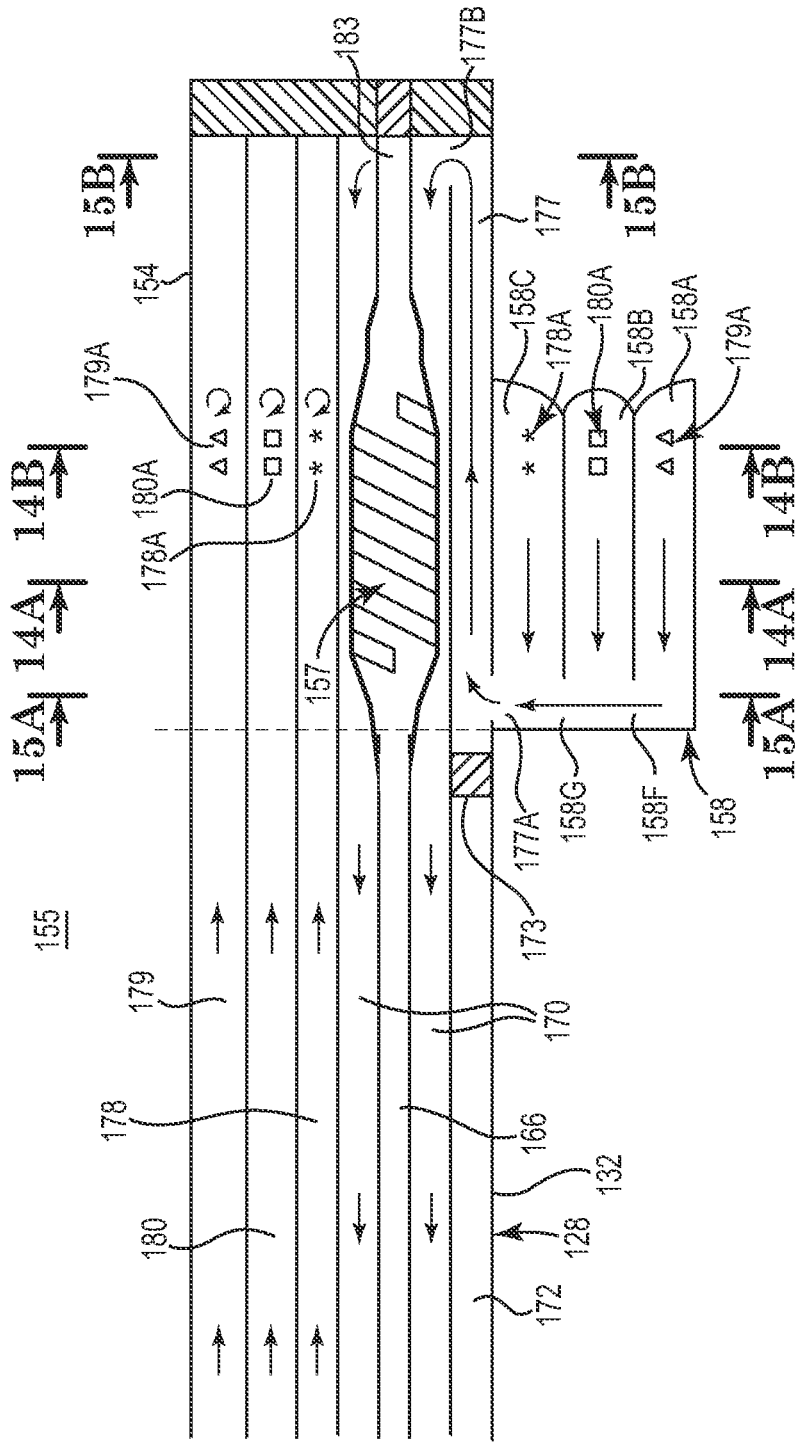
FIG. 13 is a diagram schematically illustrating a defined fluid flow path of a thermal therapy catheter, according to one embodiment of the present invention.

FIG. 13 is a diagram 155 that schematically illustrates a fluid flow path for catheter shaft 132 in the vicinity of cooling balloon 158 as cooling fluid passes through the respective lumens of catheter shaft 132 and respective lobes of balloon 158. In FIG. 13, the respective lumens and lobes are laid out in a side-by-side manner and include directional arrows that indicate a direction of fluid flow through each of the respective lumens and lobes. For the purpose of illustration, lumens 170-180 of catheter shaft 132 and multi-lobe balloon 158 is shown in FIG. 13 as being "flattened out" in two dimensions. However, it should be understood that multi-lobe balloon 158 is wrapped around catheter shaft 132 in a final assembly of the present invention, as shown in the sectional views of FIGS. 14A, 14B, 15A, and 15B. For example, while in actuality the lobes 158A-158C surround the catheter shaft 132 in a generally circular pattern, in FIG. 13, the lobes 158A-158C are illustrated in a side-by-side manner to display the lobes 158A-158C simultaneously with display of the respective lumens 170-180 of catheter shaft 132.

Figure 14B:
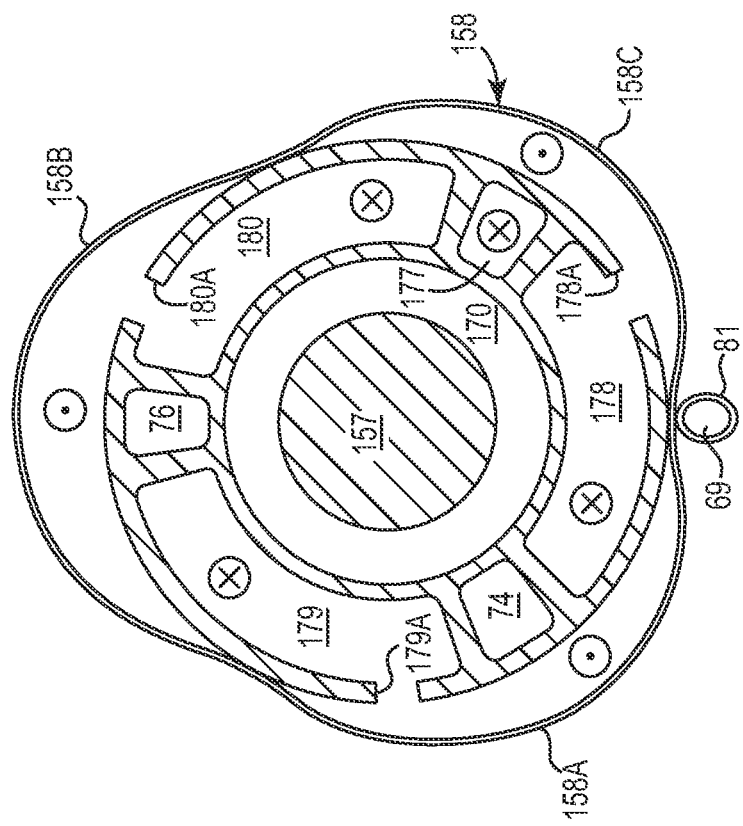
FIG. 14B is a cross-sectional view, as taken along line 14B-14B of FIG. 13, of the thermal therapy catheter, according to one embodiment of the present invention.
Figure 14A:
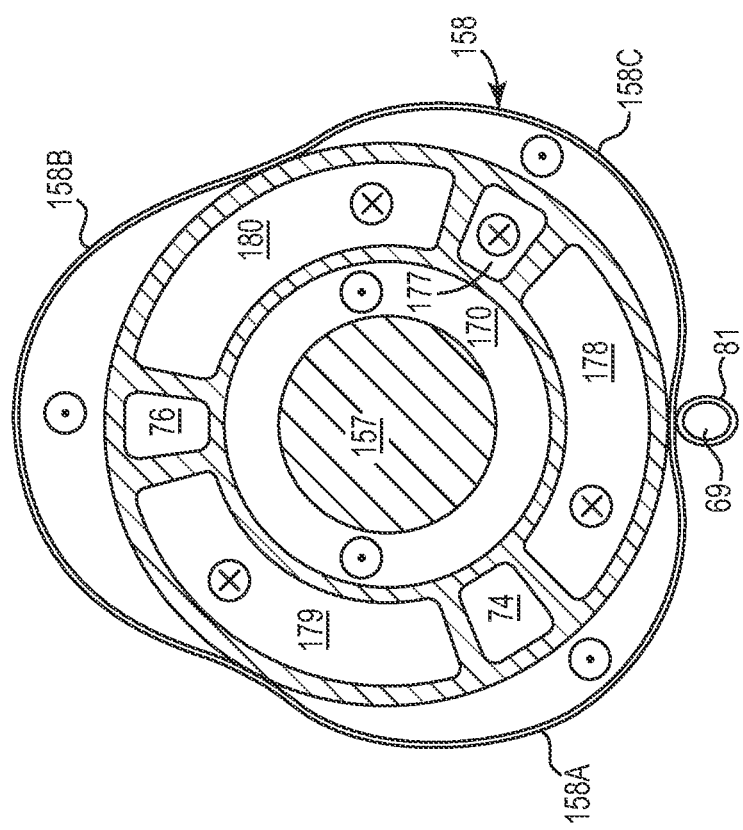
FIG. 14A is a cross-sectional view, as taken along line 14A-14A of FIG. 13, of the thermal therapy catheter, according to one embodiment of the present invention.
Figure 15B:
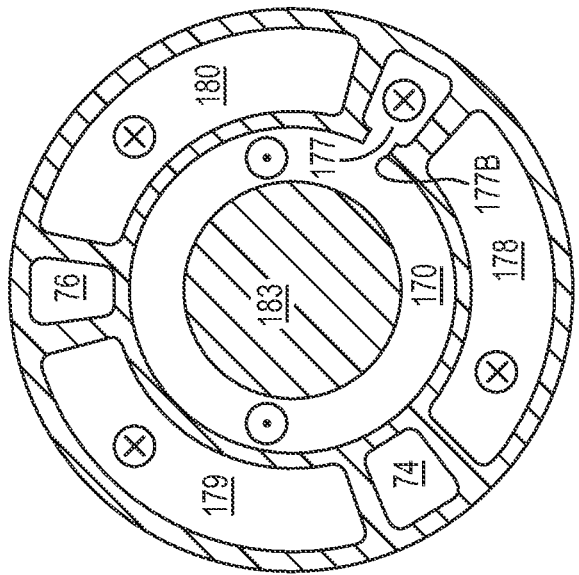
FIG. 15B is a cross-sectional view, as taken along line 15B-15B of FIG. 13, of the thermal therapy catheter, according to one embodiment of the present invention.
Figure 15A:
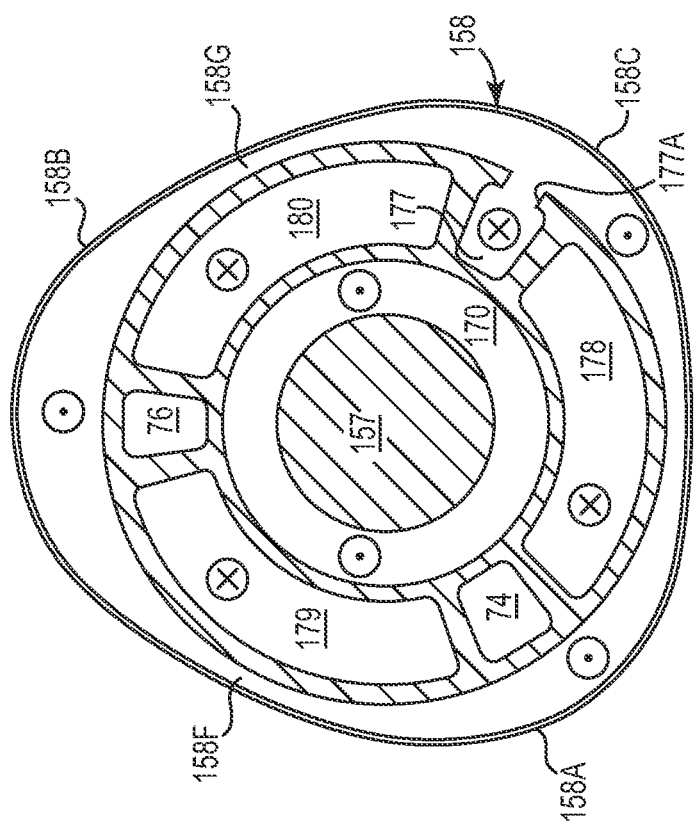
FIG. 15A is a cross-sectional view, as taken along line 15A-15A of FIG. 13, of the thermal therapy catheter, according to one embodiment of the present invention.

In addition, the cross-sectional views of FIGS. 14A, 14B, 15A, 15B, further aid in an understanding of the fluid flow path within the lumens 170-180 of catheter shaft 132 and lobes 158A-158C of balloon 158. FIG. 14A is a cross-sectional view of catheter shaft 132 taken along line 14A-14A of FIG. 13. FIG. 14B is a cross-sectional view of catheter shaft 132 taken along line 14B-14B of FIG. 13. FIG. 15A is a cross-sectional view of catheter shaft 132 taken along line 15A-15A of FIG. 13. FIG. 15B is a cross-sectional view of catheter shaft 132 taken along line 15B-15B of FIG. 13. As seen in the cross-sectional views, fluid flowing distally or toward antenna 157 of catheter 128 is represented as an "x" inside a circle, while fluid flowing proximally or away from antenna 157 is represented as a dot inside a circle.

Cooling lumens 178, 179, and 180 cooperate with cooling system 36 via ports 46 and 48 of handle 30 (FIG. 2) to provide a path for selectively controlled flow of fluid through cooling lumens 178, 179 and 180, through antenna-and-cooling lumen 170, and through lobes 158A, 158B and 158C of multi-lobe balloon 158 during a treatment session. Cooling lumens 178, 179 and 180, antenna-and-cooling lumen 170, and multi-lobe balloon 158 are designed to provide a path for the flow of fluid therethrough, providing advantageous cooling performance.

As shown in FIG. 13, the cooling fluid flows under dynamic fluid pressure simultaneously in cooling lumens 178, 179, and 180 toward distal end 54 of shaft 132, and this fluid exits the respective cooling lumens 178, 179, 180 via apertures 178A, 179A, 180A to begin a flow path through the lobes of balloon 158. In particular, cooling fluid flows from cooling lumen 178, via aperture 178A (represented as a series of asterisks), into lobe 158C of balloon 158, as shown in FIGS. 13 and 14B. At the same time, cooling fluid flows from cooling lumen 179, via aperture 179A (represented as a series of triangles), into lobe 158A while cooling fluid flows from cooling lumen 180, via aperture 180A (represented as a series of squares), into lobe 158B, as shown in FIGS. 13 and 14B. Accordingly, cooling fluid flows in the same general first direction simultaneously through all of the cooling lumens 178, 179, 180 toward distal end 154 of catheter shaft 132 with each cooling lumen 178, 179, 180 being in independent or exclusive communication with a respective one of the lobes (158C, 158A, 158B, respectively) of balloon 158. Next, cooling fluid flows in the same general second direction simultaneously through all the lobes 158A, 158B, 158C, opposite the first direction. Channels 158F and 158G connect, and establish fluid communication between, a proximal end of the respective lobes 158A, 158B, and 158C as fluid flows from the lobes 158A-158C into distal portion 177 of fiber lumen 172.

In particular, as illustrated in both FIGS. 13 and 15A, the cooling fluid exits lobe 158C of balloon 158 through aperture 177A into distal portion 177 of fiber lumen 172 of catheter shaft 132. In one aspect, distal portion 177 of fiber lumen 172 acts as an additional cooling lumen extending parallel to and adjacent the antenna 157 within antenna-and-cooling lumen 170. In addition, as illustrated in both FIGS. 13 and 15B, this distal portion 177 of fiber lumen 172 provides a passageway to fluidly communicate with antenna-and-cooling lumen 170 via aperture 177B, such that fluid flows from balloon lobe 158C, via distal portion 177, into antenna-and-cooling lumen 170. In one aspect, as fluid flows from distal portion 177 into lumen 170, the fluid flows around a distal anchor portion 183 of catheter 128, as illustrated in FIG. 13.

After fluid flows simultaneously through all the lobes 158A, 158B, 158C of balloon 158, this arrangement further directs cooling fluid to flow into and through antenna-and-cooling lumen 170 to cause the cooling fluid to surroundingly flow by and around antenna 157. In some embodiments, cooling fluid flows around antenna 157 in a manner substantially similar to that previously described in association with FIGS. 11-12. As further shown in FIG. 13, cooling lumen 170 also serves as an exhaust lumen, so that after fluid passes antenna 157 and travels proximally, the cooling fluid exits shaft 132 at proximal end 50 thereof through port 48 of handle 30 (FIG. 2) for later recirculation via cooling system 36.

The overall fluid circulation system described above is operable to circulate cooling fluid throughout cooling lumens 178, 179 and 180, antenna-and-cooling lumen 170, and multi-lobe balloon 158 in a defined fluid flow path, inflating multi-lobe balloon into contact with a wall of the urethra.

FIGS. 16-19B schematically illustrate a catheter 228, according to one embodiment of the present invention. In one embodiment, catheter comprises at least substantially the same general features and attributes as previously described for the catheter 28 in association with FIGS. 1-12 and/or FIGS. 13-15B, except for providing different fluid flow path through the respective lumens of the catheter shaft and the respective lobes of the cooling balloon. Like reference numerals denote like elements.

Figure 16:
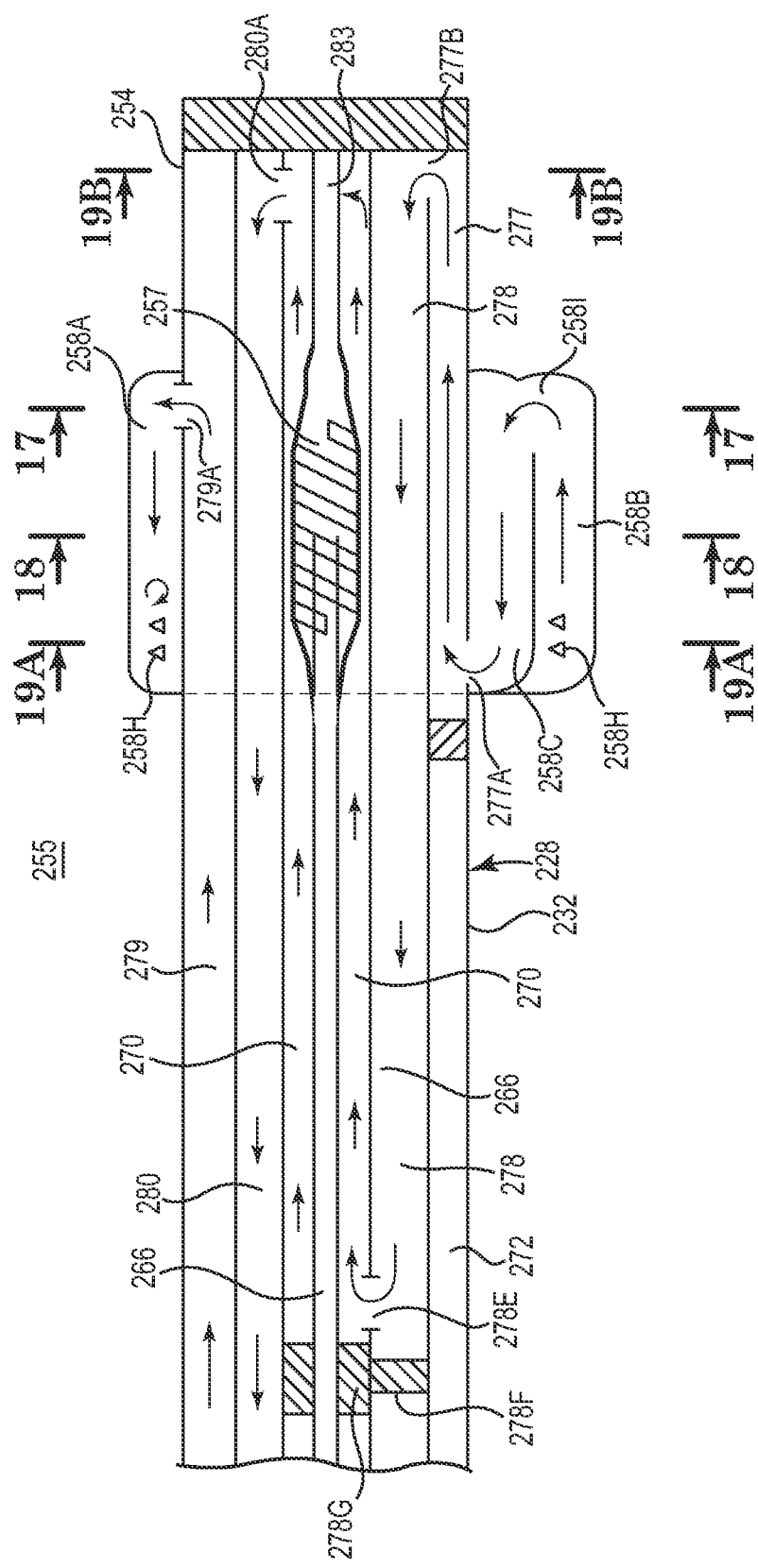
FIG. 16 is a diagram schematically illustrating a defined fluid flow path of a thermal therapy catheter, according to one embodiment of the present invention.

FIG. 16 is a diagram 255 that schematically illustrates a fluid flow path for catheter shaft 232 in the vicinity of cooling balloon 258 as cooling fluid passes through the respective lumens of catheter shaft 232 and respective lobes of balloon 258. As in the previously described embodiments, the respective lumens and lobes are laid out in a side-by-side manner and include directional arrows that indicate a direction of fluid flow through each of the respective lumens and lobes.

Figure 18:
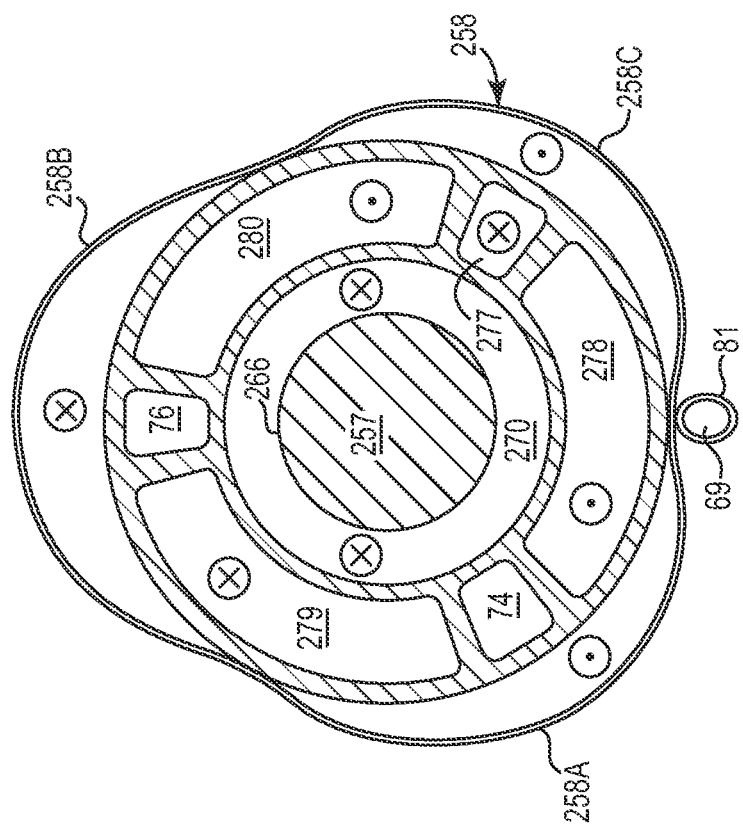
FIG. 18 is a cross-sectional view, as taken along line 18-18 of FIG. 16, of the thermal therapy catheter, according to one embodiment of the present invention.
Figure 17:
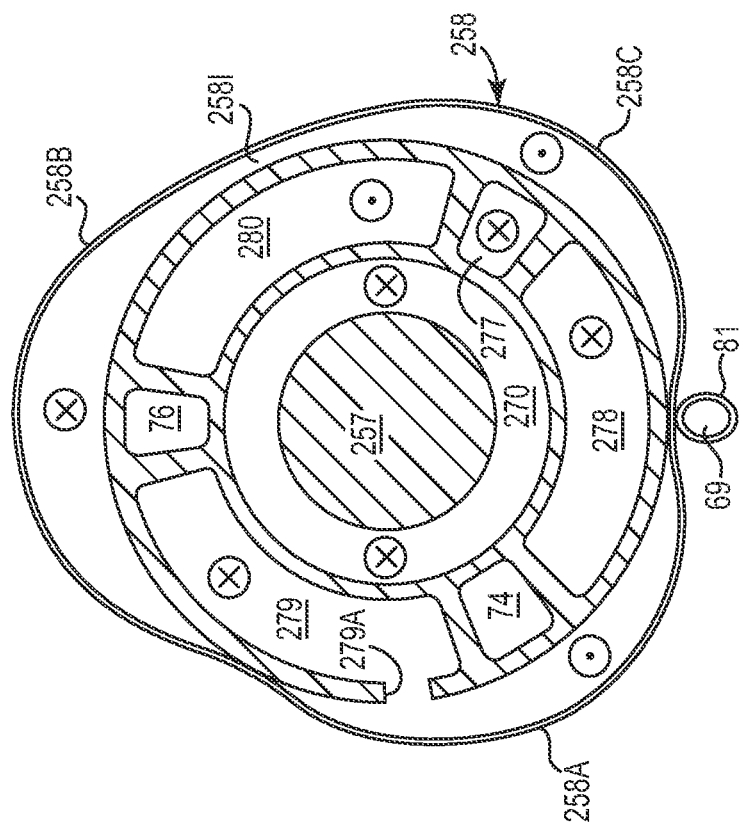
FIG. 17 is a cross-sectional view, as taken along line 17-17 of FIG. 16, of the thermal therapy catheter, according to one embodiment of the present invention.

In addition, the cross-sectional views of FIGS. 17, 18, 19A, 19B, further aid in an understanding of the fluid flow path within the lumens 270-280 of catheter shaft 232 and lobes 258A-258C of balloon 258. FIG. 17 is a cross-sectional view of catheter shaft 232 taken along line 17-17 of FIG. 16. FIG. 18 is a cross-sectional view of catheter shaft 232 taken along line 18-18 of FIG. 16. FIG. 19A is a cross-sectional view of catheter shaft 232 taken along line 19A-19A of FIG. 16. FIG. 19B is a cross-sectional view of catheter shaft 232 taken along line 19B-19B of FIG. 16. As seen in the cross-sectional views, fluid flowing distally or toward antenna 257 of catheter 228 is represented as an "x" inside a circle, while fluid flowing proximally or away from antenna 257 is represented as a dot inside a circle.

Cooling lumens 278, 279, and 280 cooperate with cooling system 36 via ports 46 and 48 of handle 30 (FIG. 2) to provide a path for selectively controlled flow of fluid through cooling lumens 278, 279 and 280, through antenna-and-cooling lumen 270, and through lobes 258A, 258B and 258C of multi-lobe balloon 258 during a treatment session. Cooling lumens 278, 279 and 280, antenna-and-cooling lumen 270, and multi-lobe balloon 258 are designed to provide a path for the flow of fluid therethrough, providing advantageous cooling performance.

In this arrangement, cooling fluid flows from cooling system 36 to cooling fluid feed line 60B and on through port 46 of handle 30 (FIG. 2) into cooling lumen 279, which serves as a fluid intake lumen. As shown in FIG. 16, the cooling fluid flows under dynamic fluid pressure in cooling lumen 279 toward distal end 254 of shaft 232, and exits cooling lumen 279 via aperture 279A to enter lobe 258A of balloon 258 (see FIG. 17) to begin a flow path through the lobes of balloon 258.

In particular, cooling fluid enters lobe 258B from lumen 279 (via aperture 258H, which is represented by a series of triangles) as shown in FIG. 16 and flows under dynamic pressure in the serpentine pattern indicated by the arrows in FIG. 16, from lobe 258B through narrow channel 258I to lobe 258C.

As illustrated in both FIGS. 16 and 19A, the cooling fluid exits lobe 258C of balloon 258 through aperture 277A into distal portion 277 of fiber lumen 272 of catheter shaft 232. In one aspect, distal portion 277 of fiber lumen 272 acts as an additional cooling lumen extending parallel to and adjacent the antenna 257 within antenna-and-cooling lumen 270. In addition, as illustrated in both FIGS. 6 and 19B, this distal portion 277 of fiber lumen 272 provides a passageway to fluidly communicate with cooling lumen 278 via aperture 277B, such that fluid flows from balloon lobe 258C, via distal portion 277, to cooling lumen 278. It will be understood that in lieu of the particular location of aperture 277B shown in FIG. 19B, other configurations can be used to form a passageway between distal portion 277 and cooling lumen 278.

As shown in FIG. 16, from aperture 277B, cooling fluid flows proximally through cooling lumen 278 toward proximal end 250 of shaft 232 until the cooling fluid exits cooling lumen 278 through aperture 278E into antenna-and-cooling lumen 270 for travel distally back toward antenna 257. In one embodiment, a plug or other barrier 278F is located proximal to aperture 278E and causes the cooling fluid to exit lumen 278 into antenna-and-cooling lumen 270. In another aspect, a plug or other barrier 278G is located proximal to aperture 278E to cause fluid entering antenna-and-cooling lumen 270 to travel distally toward antenna 257. This general arrangement directs cooling fluid through antenna-and-cooling lumen 270 to surroundingly flow by and around antenna 257 within the antenna-and-cooling lumen 270. In some embodiments, cooling fluid flows around antenna 257 in a manner substantially similar to that previously described in association with FIGS. 11-12, including the cooling fluid flowing around a distal anchor portion 283 of catheter shaft 232, as illustrated in FIG. 16.

After passing by antenna 257, the cooling fluid exits antenna-and-cooling lumen 270 via aperture 280A and enters cooling lumen 280. As further shown in FIG. 16, cooling lumen 280 serves as an exhaust lumen so that fluid traveling proximally exits shaft 232 at proximal end 250 thereof through port 48 of handle 30 (FIG. 2) for later recirculation via cooling system 36.

The overall fluid circulation system described above is operable to circulate cooling fluid throughout cooling lumens 278, 279 and 280, antenna-and-cooling lumen 270, and multi-lobe balloon 258 in a defined fluid flow path, inflating multi-lobe balloon into contact with a wall of the urethra.

It will be understood that other fluid flow configurations may be used.

FIGS. 20-25 are partial sectional views that schematically illustrate a method of constructing an antenna assembly, according to one embodiment of the present invention. In particular, starting with a completed antenna 457, this method adds an anchor configured to enable anchoring the antenna 457 relative to a catheter shaft while also providing a fluid-tight sleeve covering over antenna 457 to isolate antenna 457 from fluid flowing by and around antenna 457 within an antenna-and-cooling lumen, such as previously described in association with FIGS. 6-19B.

FIG. 20 is side elevational view of a partial antenna assembly 400, according to one embodiment of the present invention. As shown in FIG. 20, assembly 400 includes an antenna 457 extending from a cable 466 and having a distal portion 402 that extends distally from a distal end 407 of antenna 457. In some embodiments, the distal portion 402 includes an outer covering formed of a polymer such as polytetrafluoroethylene (PTFE) material, and as is commonly sold under the trademark Telfon®. In one embodiment, this outer covering takes the form of a tube or sleeve.

To form the construction shown in FIG. 20, a first tube 410 is positioned onto distal portion 402 of antenna 457. In particular, a proximal portion 412 of first tube 410 is aligned with and advanced onto distal portion 402 (as represented by directional arrow A) of antenna 457 to achieve the configuration shown in FIG. 20. In one embodiment, the tube 410 is formed of a flexible polymer, such as a polyvinylidene fluoride (PVDF) material which is commonly sold under the trademark Kynar®. The position of proximal portion 412 of first tube 410 is maintained on distal portion 402 of antenna 457 (over the first tube 405) via application of heat to cause the proximal portion 412 to heat-shrink about distal portion 402 of antenna 457. However, it will be understood that heat shrinking can be applied in a later step.

Meanwhile, as shown in FIG. 20, a distal portion of first tube 410 extends distally from a distal end of antenna 457. Adhesive 420 is filled within the lumen formed by the distal portion of the second tube 410 and then the adhesive is cured to meld adhesive 420 and second tube 410 together to achieve the configuration of partial antenna assembly 470 shown in FIG. 21. In one embodiment, adhesive comprises a commercially available medical grade adhesive, such as but not limited to Loctite® Medical Adhesive 3341.

In some embodiments, the length of distal portion of first tube 410 is selected to allow space for mounting of a silicone gasket (e.g. tube 490), for creation of separate fluid cavities within the antenna-and-cooling lumen, and to provide enough length for a sleeve (e.g. sleeve 510) to overlap the silicone gasket, and to provide an end portion suited to be adhesive secured. In some embodiments, this method further includes installing a pair of silicone tubes sized and positioned to act as gaskets to provide a fluid-tight seal on each of opposite ends of antenna 457. In particular, with reference to FIG. 22 a first silicone tube 490 (after being swelled with Heptane or another solvent) is slidably positioned at a location spaced apart from and proximal to proximal end 409 of antenna 457. In addition, a second silicone tube 482 (after being swelled with Heptane) is slidably advanced over second tube 410 and positioned to be just distal of a shoulder 485 at the transition that distal portion 412 of second tube 410 tapers beyond the end of distal portion 402 of antenna 457. After the silicone tubes 482, 490 are positioned as desired, they become fixed in place via shrinking as the solvent evaporates from the respective tubes.

Figure 22:
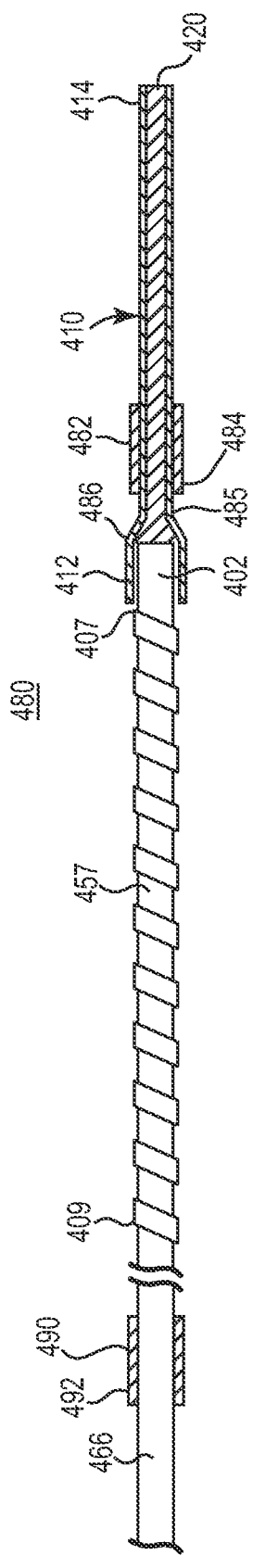
Figure 23:
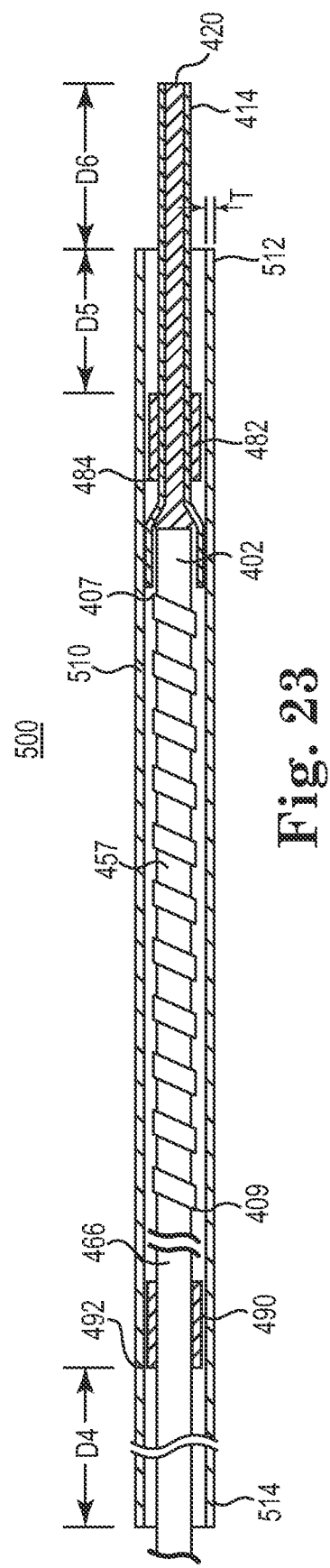

With both silicone tubes 490 and 482 in position as shown in FIG. 22, an elongate sleeve 510 is slidably advanced and positioned to extend over antenna 457 as shown in FIG. 23. In one aspect, sleeve 510 has a length such that its distal end 512 extends distally beyond a distal end of silicone tube 482 and its proximal end 514 extends proximally beyond a proximal end 492 of silicone tube 490. Accordingly, sleeve 510 has a length substantially greater than a length of the antenna 457. In one embodiment, the proximal end 514 of sleeve 510 extends at least about 0.2 inches (as represented by D4) proximally beyond proximal end 492 of silicone tube 490.

In another aspect, distal end 512 of sleeve 510 extends distally beyond a distal end 483 of silicone tube 482 by a distance D5 such that distal end 512 of sleeve 510 terminates a distance D6 from a proximal end 414 of partial antenna assembly 500, as shown in FIG. 23. In one embodiment, sleeve 510 is formed from a fluoropolymer, such as but not limited to, fluorinated ethylene propylene (FEP). In one embodiment, distance D5 is about 0.2 inches and distance D6 is about 0.2 inches.

Figure 24:
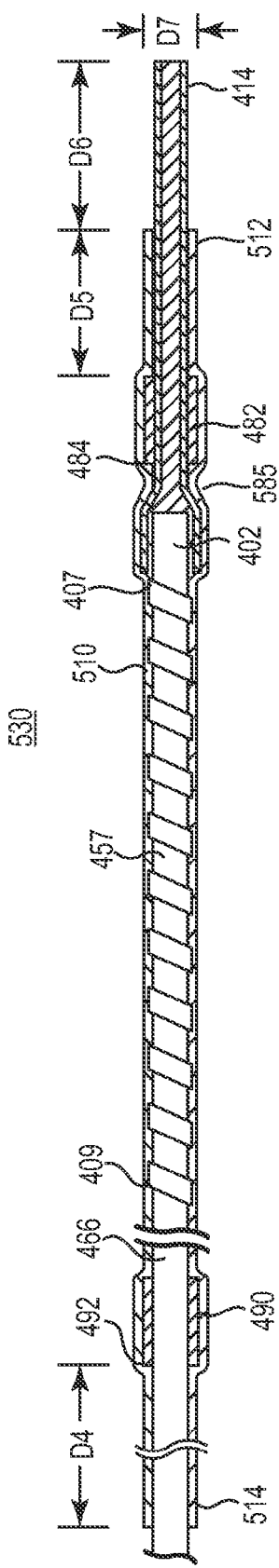

With sleeve 510 positioned as described and illustrated in FIG. 23, heat is applied to shrink sleeve 510 about the enclosed components, securing the sleeve 510 and the contained components, resulting in the configuration of partial antenna assembly 530 shown in FIG. 24. It will be understood that some components of assembly 530 are generally enlarged for illustrative purposes.

In addition, embodiments of the present invention also recognize that the specific absorption rate (SAR) for a dipole antenna can be balanced by changing a thickness of a near field material, such as the sleeve that covers the coils of the antenna. Accordingly, this ability allows the antenna to be configured with a single pitch winding of its coils, rather than variable or multiple pitch windings saving time and money in manufacturing because the pitch no longer need be used to control balance of the SAR field. This arrangement also ameliorates the prior need to identify an optimal transition point at which the coil windings begin a different pitch. Moreover, in some embodiments, a greater pitch is employed, thereby permitting a shorter length of material to be used to form the coil windings for a given axial length of the antenna, if desired.

In some embodiments, a dielectric property or parameter of the sleeve 510 is selected in order to produce a desired type of SAR field. In one example, the sleeve is formed of a fluoropolymer material and has a generally uniform thickness. For example, a sleeve formed of material having a first dielectric parameter is configured to yield a generally symmetric specific absorption rate field. On the other hand, a sleeve formed of material having a second dielectric parameter (less than the first dielectric parameter) yields a first asymmetric specific absorption rate field having a greater near field specific absorption rate in a distal direction relative to a transition point of the coil windings. Alternatively, a sleeve formed of a material having a third dielectric parameter (greater than the first dielectric parameter) yields a second asymmetric specific absorption rate field having a greater near field specific absorption rate in a proximal direction relative to a transition point of the coil windings.

Similarly, one can achieve a desired SAR field by selecting one of several different thicknesses of the sleeve. For example, a sleeve formed of material having a first thickness is configured to yield a generally symmetric specific absorption rate field. On the other hand, a sleeve formed of material having a second thickness less than the first thickness yields a first asymmetric specific absorption rate field having a greater near field specific absorption rate in a distal direction relative to a transition point of the coil windings. Alternatively, a sleeve formed of a material having a third thickness greater than the first thickness yields a second asymmetric specific absorption rate field having a greater near field specific absorption rate in a proximal direction relative to a transition point of the coil windings.

Figure 25:
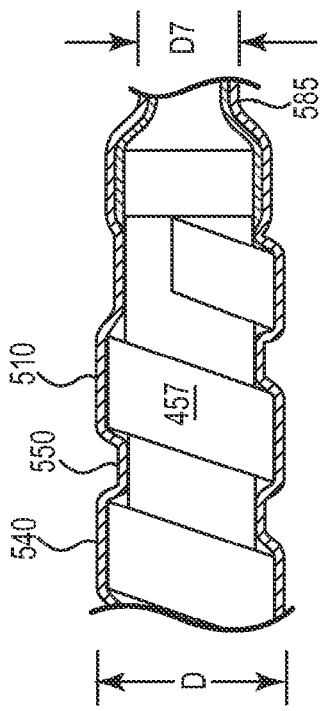
FIG. 25 is a partial sectional view of an antenna assembly including a distal anchor portion extending therefrom, according to one embodiment of the present invention.

FIG. 25 is an enlarged partial view of a segment of antenna 457 taken from FIG. 24, and which illustrates the manner in which sleeve 510 sealingly fits about antenna 457. As shown in FIG. 25, sleeve 510 follows the cross-sectional contour of antenna 457 so that when covered with sleeve 510, antenna 457 defines recesses 550 between adjacent windings 130 of antenna 457. In some embodiments, at least the recesses 550 facilitate flow of cooling fluid around and along antenna 457 within an antenna-and-cooling lumen in manner substantially similar as the embodiments previously described in association with FIGS. 11-12.

Moreover, a thickness of the sleeve covering is selectable to match a length of the antenna to achieve the desired SAR field and/or to achieve a uniform or intentionally asymmetric SAR field. For example, a generally thinner sleeve covering tends to produce greater SAR components on a driven element of a dipole antenna (relative to the non-drive element) while a generally thicker sleeve covering tends to produce greater SAR components on a non-driven element of a dipole antenna (relative to the driven element). By accounting for factors such as the length of the antenna coil, its pitch, and the dielectric properties of the sleeve covering, one can select a thickness of the sleeve covering to produce a desired SAR field for a given antenna. Similarly, selection of the thickness of the sleeve covering, while accounting for other factors (e.g. pitch, tap point location, matching capacitor value) of the antenna, allows one to achieve a desired resonant frequency simultaneously with a desired SAR field.

Embodiments of the present invention provide an improved thermal therapy catheter designed to enhance the efficiency of treatment of diseased tissue from an adjacent body lumen, particularly for treatment of diseased prostate tissue from an urethrally inserted applicator. A multi-lobe balloon is attached around the catheter shaft, with interiors of the balloon lobes in communication with cooling lumens of the catheter, so that circulation of fluid in the cooling lumens dynamically inflates the balloon lobes. As a result, the balloon lobes come into full contact with the wall of the urethra, and the cooling fluid circulating in the balloon lobes is thereby able to efficiently conduct heat away from the urethral wall tissue to preserve the urethra while delivering microwave energy to heat prostate tissue to high temperatures for a sufficient time (such as above about 45° C. for about one hour, or about 50° C. for about 30 minutes) to necrose the targeted prostate tissue. Implementing a multi-lobe cooling balloon around the catheter shaft that provides a very small wall thickness between the actual cooling fluid and the urethral wall, further enhancing the effects of cooling. In one embodiment, the balloon wall thickness is about 0.002 inches. In addition, a cross-linked material is utilized in an exemplary embodiment of the invention so that the multi-lobe balloon is made substantially non-distensible and a repeatable inflated diameter may be achieved in the multi-lobe balloon, with an inflated diameter of about 24 French in one embodiment.

The arrangement and shape of the lumens in the catheter shaft is also designed for efficient operation of the thermal therapy catheter system. As shown in at least FIGS. 5 and 7-9, temperature sensing fiber lumen 72, urine drainage lumen 74 and balloon inflation lumen 76 are all formed with generally trapezoidal cross-sections, so as to minimize the included angle of each of these lumens. As a result, the included angle of cooling lumens 78, 79 and 80 is maximized, improving the efficiency of urethral cooling. In addition, lobes 58A, 58B and 58C of multi-lobe balloon 58 are formed with three seams between the respective lobes. Therefore, there is a potential for "hot spots" in the urethral wall at these seams. To allay this potential difficulty, cooling lumens 78, 79 and 80 are specifically designed so as to be located adjacent to those seams, thereby providing sufficient cooling of the urethral wall at the seams of multi-lobe balloon 58 in addition to the inflated lobes of the balloon. Cooling lumens 78, 79 and 80 also extend along the entire length of the microwave antenna to provide internal cooling of the catheter and thereby ensure that the thermoplastic material of the catheter shaft is not affected by the resistive heating produced by the antenna and the heating produced by absorption of microwave energy by the catheter walls. Furthermore, the fluid flow path in embodiments of the present invention provides that cooling fluid is flowing in at least one cooling lumen (such as in cooling lumens 78 and 80) adjacent to retention balloon 56 to cool the fluid in retention balloon 56, flowing in all of cooling lumens 78, 79 and 80 adjacent to microwave antenna 57, and flowing in antenna-and-cooling lumen 70, to ensure that the cooling fluid is able to have its maximum cooling effect on the catheter walls adjacent to microwave antenna 57 and directly on antenna 57 (via antenna-and-cooling lumen 70).

It should be understood that while the present invention has been described with respect to selected embodiments, minor modifications may be made to certain details of the catheter designs shown while still practicing the principles and teachings of the present invention. For example, while specific lumen shapes and sizes have been disclosed, other shapes and sizes are contemplated by the present invention, while practicing the teachings of the invention relating to the motivation for relative lumen positioning and the like.

It is to be understood that the features of the various exemplary embodiments described herein may be combined with each other, unless specifically noted otherwise.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A device for treating tissue adjacent to a body lumen, the device comprising:
   a catheter shaft insertable into the body lumen and including a plurality of cooling lumens arranged generally circumjacent a generally central lumen, wherein at least some of the circumjacent cooling lumens are in fluid communication with the central lumen; and
   an energy emitting assembly including a proximal portion, a microwave antenna, and a distal portion extending distally from the microwave antenna, wherein the energy emitting assembly extends through the central lumen, and wherein the microwave antenna comprises a helical dipole configuration that includes a core extending along a length of at least the energy emitting portion, a series of coil windings arranged in a helical pattern about the core, and a sleeve covering at least the coil windings,
   wherein the series of coil windings defines a series of recesses between the adjacent coil windings, and wherein the respective coil windings are in contact against the wall of the central lumen to define a generally helical flow path via at least some of the recesses along a length of the microwave antenna.

2. A device for treating tissue adjacent to a body lumen, the device comprising:
   a catheter shaft insertable into the body lumen and including a plurality of cooling lumens arranged generally circumjacent a generally central lumen, wherein at least some of the circumjacent cooling lumens are in fluid communication with the central lumen; and
   an energy emitting assembly including a proximal portion, an energy emitting portion, and a distal portion extending distally from the energy emitting portion, wherein the energy emitting assembly extends through the central lumen without contact between at least the energy emitting portion and a wall of the central lumen to direct a flow of cooling fluid directly about an outer surface of the energy emitting portion within the central lumen,
   wherein the energy emitting portion includes a cover extending over and along at least an entire length of the energy emitting portion to sealingly isolate the energy emitting portion from the circulating cooling fluid,
   wherein the cover includes:
      a first tube formed having a generally uniform thickness;
      a second tube positioned proximal to, and spaced apart from, a proximal end of the energy emitting portion, the second tube secured about a proximal portion of the energy emitting assembly; and
      a third tube positioned distal to, and spaced apart from, a distal end of the energy emitting portion, the third tube secured about the distal portion of the energy emitting assembly,
      wherein the first tube has a length extending substantially greater than a length of the energy emitting portion, with a proximal end of the first tube extending proximally beyond the second tube and a distal end of the first tube extending distally beyond the third tube.

3. The device of claim 2, wherein the first tube is formed of a fluoropolymer material and the respective second and third tubes are formed of a silicone material.

4. A device for treating tissue adjacent to a body lumen, the device comprising:
- a catheter shaft insertable into the body lumen and including a plurality of cooling lumens arranged generally circumjacent a generally central lumen, wherein at least some of the circumjacent cooling lumens are in fluid communication with the central lumen; and
- an energy emitting assembly including a proximal portion, an energy emitting portion, and a distal portion extending distally from the energy emitting portion, wherein the energy emitting assembly extends through the central lumen without contact between at least the energy emitting portion and a wall of the central lumen to direct a flow of cooling fluid directly about an outer surface of the energy emitting portion within the central lumen, wherein the energy emitting portion includes a microwave antenna, and
- wherein the distal portion of the energy emitting assembly defines an anchor portion having a diameter less than a diameter of the energy emitting portion to permit the circulating cooling fluid to flow by and around the anchor portion, and wherein the anchor portion includes a distal tip secured to a portion of the catheter shaft at a location spaced apart distally from the energy emitting portion to define a passageway, and at least some of the respective cooling lumens fluidly communicate with the central lumen via the passageway.

5. A device for treating tissue adjacent to a body lumen, the device comprising:
- a catheter shaft insertable into the body lumen and including a plurality of cooling lumens arranged generally circumjacent a generally central lumen, wherein at least some of the circumjacent cooling lumens are in fluid communication with the central lumen; and
- an energy emitting assembly including a proximal portion, an energy emitting portion, and a distal portion extending distally from the energy emitting portion, wherein the energy emitting assembly extends through the central lumen without contact between at least the energy emitting portion and a wall of the central lumen to direct a flow of cooling fluid directly about an outer surface of the energy emitting portion within the central lumen,
- wherein the plurality of cooling lumens includes at least an intake cooling lumen and an exhaust cooling lumen, both configured to be in fluid communication with an external cooling fluid unit, and
- wherein the device includes a cooling balloon connected to an exterior of the catheter shaft adjacent the energy emitting portion, the cooling balloon being in communication with the central lumen and the central lumen in communication with the exhaust cooling lumen,
- wherein the device includes an auxiliary lumen configured to establish communication between the cooling balloon and the central lumen, the auxiliary lumen is arranged with the cooling lumens to be circumjacent the central lumen, and
- wherein the auxiliary lumen comprises a proximal portion and a distal portion separated from the proximal portion by a plug to sealingly isolate the distal portion from the proximal portion, the distal portion positioned adjacent the energy emitting portion and configured to communicate fluid from the balloon to the central lumen.

6. The device of claim 5, wherein the proximal portion of the auxiliary lumen comprises a temperature sensing fiber lumen.

7. The device of claim 5, wherein the cooling balloon comprises a multi-lobe balloon including a plurality of lobes arranged circumferentially about the catheter shaft, wherein a first respective one of the lobes is in communication with the intake cooling lumen to receive cooling fluid into the balloon and a second respective one of the lobes is in communication with the auxiliary lumen, with the respective lobes configured to allow flow of cooling fluid through all of the respective lobes prior to exiting the balloon.

8. The device of claim 7, wherein the respective lobes of the balloon are configured to define the fluid flow path through the respective lobes of the cooling balloon in a serpentine path.

9. The device of claim 8, wherein respective cooling lumens and the central lumen are configured to further define the fluid flow path in a serpentine path through the cooling lumens and the central lumen of the catheter shaft.

10. A device for treating tissue adjacent to a body lumen, the device comprising:
- a catheter shaft insertable into the body lumen and including a plurality of cooling lumens arranged generally circumjacent a generally central lumen, wherein at least some of the circumjacent cooling lumens are in fluid communication with the central lumen; and
- an energy emitting assembly including a proximal portion, an energy emitting portion, and a distal portion extending distally from the energy emitting portion, wherein the energy emitting assembly extends through the central lumen without contact between at least the energy emitting portion and a wall of the central lumen to direct a flow of cooling fluid directly about an outer surface of the energy emitting portion within the central lumen,
- wherein the plurality of cooling lumens includes several cooling lumens arranged in parallel and configured as independent intake lumens to communicate with and receive cooling fluid from an external cooling fluid unit,
- wherein the device includes a cooling balloon connected to an exterior of the catheter shaft adjacent the energy emitting portion, the cooling balloon in communication with the respective intake cooling lumens to receive cooling fluid and in communication with the central lumen via an auxiliary lumen to release cooling fluid, wherein the central lumen defines an exhaust lumen configured to communicate cooling fluid to the external cooling fluid unit, and
- wherein the auxiliary lumen is arranged with the cooling lumens to be circumjacent the central lumen and the auxiliary lumen comprises a proximal portion and a distal portion sealingly isolated from the proximal portion, the distal portion positioned adjacent the energy emitting portion and configured to communicate fluid from the balloon to the central lumen.

11. The device of claim 10, wherein the proximal portion of the auxiliary lumen comprises a temperature sensing fiber lumen.

12. A device for treating tissue adjacent to a body lumen, the device comprising:
- a catheter shaft insertable into the body lumen and including a plurality of cooling lumens arranged generally circumjacent a generally central lumen, wherein at least some of the circumjacent cooling lumens are in fluid communication with the central lumen;
- an energy emitting assembly extending through the central lumen and including an energy emitting portion and an anchor portion extending distally from the energy emitting portion, wherein the anchor portion secures the energy emitting assembly within the catheter shaft, and wherein the central lumen and the energy emitting portion are configured to direct a flow of cooling fluid about an outer surface of the energy emitting portion within the central lumen, wherein the anchor portion is configured to permit cooling fluid that communicates between the central lumen and the respective cooling lumens to flow by and around the anchor portion within the central lumen, wherein the anchor portion includes:
a first tube including a proximal portion secured relative to the distal portion of the energy emitting portion and a distal portion extending distally from the energy emitting portion, wherein the distal portion of the first tube defines a lumen containing an adhesive material
a second tube secured about the distal portion of the first tube and positioned distal to the distal end of the energy emitting portion;
a third tube secured about a shaft of the energy emitting assembly proximal to, and spaced apart from, a proximal end of the energy emitting portion; and
a fourth tube having a length extending substantially greater than a length of the energy emitting portion, with a proximal end of the fourth tube extending proximally beyond the third tube and a distal end of the fourth tube extending distally beyond the second tube, wherein the fourth tube has a length substantially greater than an entire length of the energy emitting portion to sealingly isolate the energy emitting portion from the circulating cooling fluid.

13. The device of claim 12, wherein the respective second and third tubes are formed of a silicone material and the fourth tube is formed of a fluorinated ethylene propylene material, and the respective tubes are secured relative to the energy emitting portion and relative to each other.

14. A device for treating tissue adjacent to a body lumen, the device comprising:
a catheter shaft insertable into the body lumen and including a plurality of cooling lumens arranged generally circumjacent a generally central lumen, wherein at least some of the circumjacent cooling lumens are in fluid communication with the central lumen, wherein the respective cooling lumens includes at least an intake cooling lumen and an exhaust cooling lumen and the central lumen is in communication with the exhaust cooling lumen, both the respective intake and exhaust cooling lumens configured to be in fluid communication with an external cooling fluid unit, and wherein the catheter shaft includes an auxiliary lumen;
a cooling balloon connected to an exterior of the catheter shaft and in communication with the central lumen via the auxiliary lumen and in communication with the intake lumen; and
an energy emitting assembly extending through the central lumen and including an energy emitting portion,
wherein the central lumen and the energy emitting portion are configured to direct a flow of cooling fluid about an outer surface of the energy emitting portion within the central lumen,
wherein the auxiliary lumen is arranged adjacent the cooling lumens to be circumjacent the central lumen, and
wherein the auxiliary lumen comprises a proximal portion and a distal portion separated from the proximal portion by a plug to sealingly isolate the distal portion from the proximal portion, the distal portion positioned adjacent the energy emitting portion and configured to communicate fluid from the balloon to the central lumen.

15. The device of claim 14, wherein the proximal portion of the auxiliary lumen comprises a temperature sensing fiber lumen.

16. The device of claim 14, wherein the cooling balloon comprises a multi-lobe balloon including a plurality of lobes arranged circumferentially about the catheter shaft, wherein the a first respective one of the lobes is in communication with the intake cooling lumen to receive cooling fluid into the balloon and a second respective one of the lobes is in communication with the auxiliary lumen, with the respective lobes configured to allow flow of cooling fluid through all of the respective lobes prior to exiting the balloon.

17. The device of claim 16, wherein the respective lobes of the balloon are configured to define the fluid flow path through the respective lobes of the cooling balloon in a serpentine path.

18. The device of claim 17, wherein respective cooling lumens and the central lumen are configured to further define the fluid flow path in a serpentine path through the cooling lumens and the central lumen of the catheter shaft.

19. The device of claim 14, wherein the energy emitting assembly comprises:
an anchor portion extending distally from the energy emitting portion within the central lumen to secure the energy emitting assembly within the catheter shaft while permitting cooling fluid that communicates between the central lumen and the respective cooling lumens to flow by and around the anchor portion.

20. A device for treating tissue within a body, the device comprising:
an energy emitting assembly including a shaft and a microwave antenna extending distally from the shaft; and
a sealing mechanism covering the microwave antenna to sealingly isolate the microwave antenna from a fluid-filled environment within a catheter, the sealing mechanism including:
a first tube secured relative to the energy emitting assembly in a position proximal to, and spaced apart from, a proximal end of the microwave antenna;
a second tube secured relative to the energy emitting assembly in a position distal to, and spaced apart from, a distal end of the microwave antenna; and
a tubular sleeve having a length extending substantially greater than a length of the microwave antenna, the tubular sleeve secured against the microwave antenna over both the respective first and second tubes, wherein a proximal end of the tubular sleeve extends proximally beyond the first tube and a distal end of the tubular sleeve extends distally beyond the second tube,
wherein the respective tubes are secured relative to the microwave antenna and relative to each other, and wherein the tubular sleeve is secured over the respective first and second tubes and secured relative to an entire length of the microwave antenna via heat shrinking.

21. The device of claim 20, wherein the tubular sleeve comprises a dielectric material having a generally uniform thickness.

22. The device of claim 21, wherein the respective first and second tubes are formed of a silicone material and the tubular sleeve is formed of a fluorinated ethylene propylene material.

23. The device of claim 20, wherein the microwave antenna comprises a dipole configuration including a core and a series of coil windings arranged about the core.

24. The device of claim 20, wherein the device includes:
a catheter shaft insertable into the body of a patient and including at least a first lumen through which the microwave antenna extends, wherein the first lumen and the microwave antenna are configured to receive and direct a flow of cooling fluid about an outer surface of the microwave antenna within the first lumen.

25. The device of claim 24, wherein the catheter shaft is sized to be inserted within a lumen of the body, and wherein the lumen is adjacent the tissue to be treated by energy emitted from the microwave antenna.

26. The device of claim 25, wherein the catheter shaft comprises:
a plurality of cooling lumens extending generally parallel to the first lumen, wherein at least some of the cooling lumens are in fluid communication with the first lumen to facilitate circulation of cooling fluid through the first lumen while applying treatment to the tissue to be treated.

* * * * *